US009125624B2

(12) United States Patent  (10) Patent No.: US 9,125,624 B2
Dekel et al.  (45) Date of Patent: Sep. 8, 2015

(54) METHOD AND APPARATUS FOR AUTOMATED REGISTRATION AND POSE TRACKING

(75) Inventors: Doron Dekel, Toronto (CA); Ahmad Kolahi, Toronto (CA); Arish Qazi, Oakville (CA)

(73) Assignee: CLARONAV INC., North York, Ontario (CA)

( * ) Notice: Subject to any disclaimer, the term of this patent is extended or adjusted under 35 U.S.C. 154(b) by 247 days.

(21) Appl. No.: 13/884,128

(22) PCT Filed: Nov. 23, 2011

(86) PCT No.: PCT/CA2011/001294
§ 371 (c)(1),
(2), (4) Date: Aug. 15, 2013

(87) PCT Pub. No.: WO2012/068679
PCT Pub. Date: May 31, 2012

(65) Prior Publication Data
US 2013/0322719 A1  Dec. 5, 2013

Related U.S. Application Data

(60) Provisional application No. 61/416,552, filed on Nov. 23, 2010.

(51) Int. Cl.
*G06K 9/00* (2006.01)
*A61B 6/00* (2006.01)
(Continued)

(52) U.S. Cl.
CPC . *A61B 6/583* (2013.01); *A61B 6/12* (2013.01); *A61B 19/54* (2013.01); *A61B 6/582* (2013.01);
(Continued)

(58) Field of Classification Search
CPC .................................................. A61B 6/583
USPC ................................................ 382/128–132
See application file for complete search history.

(56) References Cited

U.S. PATENT DOCUMENTS 7,319,781 B2 *  1/2008  Chen et al. .................... 382/128
7,702,380 B1    4/2010  Dean
(Continued)

OTHER PUBLICATIONS

International Search Report, PCT/CA2011/001294, mailed on Feb. 3, 2012.
(Continued)

*Primary Examiner* — Shefali Goradia

(57) ABSTRACT

Method and apparatus are described herein for registering an anatomical region with a scanned image of the anatomical region. The method includes pressing a moldable appliance against a surface of the anatomical region or a facsimile thereof to provide an intermediate appliance; hardening the intermediate appliance to provide the formed appliance; providing a fiducial body attached to the formed appliance; attaching the formed appliance with the fiducial body attached thereto to the anatomical region; scanning the anatomical region with the formed appliance attached thereto and the fiducial body attached to the formed appliance to obtain a three-dimensional volume representation of the fiducial body and an interior of the anatomical region; segmenting the part of the fiducial body in the three-dimensional volume representation to obtain a segmented fiducial body region; aligning the segmented fiducial body region with a reference model of the fiducial body to obtain a mapping transformation; and operating a data processor to map locations in an interior of the anatomical region to corresponding locations in the three-dimensional volume representation of the interior of the anatomical region based on the mapping transformation. The apparatus may include a moldable appliance configured for molding into a formed appliance and a fiducial body being attached to the moldable appliance, wherein the fiducial body is scan detectable entirely or in part, shaped such that an orientation of the fiducial body relative the anatomical region is uniquely determinable, and rigidly fixed to the formed appliance such that the fiducial body is in a fixed spatial relationship with the formed appliance.

22 Claims, 18 Drawing Sheets

(51) Int. Cl.
 *A61B 6/12* (2006.01)
 *A61B 19/00* (2006.01)
 *A61B 17/00* (2006.01)

(52) U.S. Cl.
 CPC .......... *A61B 2017/00946* (2013.01); *A61B 2017/00955* (2013.01); *A61B 2019/5255* (2013.01); *A61B 2019/5265* (2013.01); *A61B 2019/5272* (2013.01); *A61B 2019/5287* (2013.01); *A61B 2019/5483* (2013.01)

(56) References Cited

U.S. PATENT DOCUMENTS 8,290,305 B2 * 10/2012 Minear et al. ............... 382/294

2007/0196007 A1 * 8/2007 Chen et al. ............... 382/131
2008/0205716 A1 * 8/2008 Von Berg et al. ............ 382/128

OTHER PUBLICATIONS

Written Opinion of the International Searching Authority, PCT/CA2011/001294, mailed on Feb. 3, 2012.

Zhang et al., "Effect of Fiducial Configuration on Target Registration Error in Image-Guided Surgery—A Experiment Study", IEEE 3rd International Conference on Biomedical Engineering and Informatics, Yantai, china, pp. 1477-1481, Oct. 2010. Full document.

Hamming et al., "Effect of Fiducial Configuration on Target Registration Error in Intraoperative Cone-Beam CT Guidance of Head and Neck Surgery", 30th Annual International IEEE EMBS Conference, Vancouver, Canada, pp. 3643-3648, Aug. 2008. Full document.

* cited by examiner

*200*

| providing at least one trackable marker, wherein the at least one trackable marker is attached to the fiducial body and wherein a spatial relationship of the at least one trackable marker to the fiducial body is known | 210 |

↓

| operating a tracking apparatus to dynamically determine a pose of the at least one trackable marker | 220 |

↓

| measuring the pose of the fiducial body based on the pose of the at least one trackable marker | 230 |

Fig. 2

METHOD AND APPARATUS FOR AUTOMATED REGISTRATION AND POSE TRACKING

RELATED APPLICATIONS

This application is a national phase entry of PCT/CA2011/001294, filed on Nov. 23, 2011, which claims priority from U.S. provisional patent application Ser. No. 61/416,552, filed on Nov. 23, 2010, the contents of each of these applications being incorporated herein by reference in their entirety.

FIELD

The described embodiments relate to the field of medicine, in particular the field of image-guided therapy.

BACKGROUND

Image-guided procedures are becoming increasingly popular in the field of medicine. Image-guided procedures, such as image-guided surgeries, generally make use of tracked surgical instruments and tracked locations on a patient's body in conjunction with corresponding three-dimensional volume images, thereby making the surgical process more accurate and less invasive.

Before an image-guided procedure commences, registration between the anatomical region to be operated upon and its pre-acquired image is performed. This registration is a process of estimating an optimal transformation, or coordinate mapping, between two different reference coordinate systems or frames: one in which image locations are specified and the other in which locations in the anatomical regions are specified.

SUMMARY

In a first aspect, some embodiments provide a method for registering an anatomical region with a scanned image of the anatomical region, the method comprising:
  pressing a mouldable appliance against a surface of the anatomical region or a facsimile thereof to shape the mouldable appliance to conform to a surface geometry of the anatomical region to provide an intermediate appliance;
  hardening the intermediate appliance to retain an appliance geometry shaped to mate with the surface geometry of the anatomical region to provide the formed appliance, wherein the formed appliance resists deformation;
  providing a fiducial body attached to the formed appliance such that the fiducial body is rigidly fixed to the formed appliance and is configured to be scannable to provide a three-dimensional volume representation of the fiducial body distinguishable from a three-dimensional volume representation of the anatomical region and the fiducial body being shaped and attached to the formed appliance such that the orientation of the fiducial body is uniquely determinable based at least in part on a degree of asymmetry of the fiducial body;
  attaching the formed appliance with the fiducial body attached thereto to the anatomical region such that when attached to the anatomical region the formed appliance resists displacement relative to the anatomical region;
  scanning the anatomical region with the formed appliance attached thereto and the fiducial body attached to the formed appliance to obtain a three-dimensional volume representation of at least a part of the fiducial body and an interior of the anatomical region in a scanned image;
  segmenting the part of the fiducial body in the three-dimensional volume representation of the at least a part of the fiducial body in the scanned image to obtain a segmented fiducial body region;
  aligning the segmented fiducial body region with a reference model of the fiducial body to obtain a mapping transformation; and
  operating a data processor to map locations in an interior of the anatomical region to corresponding locations in the three-dimensional volume representation of the interior of the anatomical region based on the mapping transformation.

The method may further comprise, when the formed appliance is mated with the surface of the anatomical region, positioning an instrument to point to locations in the interior of the anatomical region, operating a pose-tracking apparatus to measure the pose of the instrument relative to the fiducial body, and operating a data processor to mark the locations pointed to by the instrument on the three-dimensional volume representation of the interior of the anatomical region based on the mapping transformation.

In some embodiments, the formed appliance may be separated from the anatomical region following the scanning and repositioned to mate the surface of the anatomical region prior to positioning the instrument. In some other embodiments, the formed appliance may remain attached to the anatomical region following the scanning.

The method may further comprise, providing at least one trackable marker, wherein the at least one trackable marker is attached to the fiducial body; and wherein the spatial relationship of the at least one trackable marker to the reference model of the fiducial body is stored in a format accessible to the data processor; and the data processor uses this spatial relationship in marking the locations.

Aligning of the segmented fiducial body region with a reference model of the fiducial body to obtain a mapping transformation may comprise operating a data processor to execute an algorithm for registration of volume-occupying regions. Such algorithm for registration of volume-occupying regions may include surface-to-surface registration algorithm, a volume-to-volume registration algorithm, a volume-to-surface registration algorithm or a feature-matching registration algorithm.

In some embodiments, the trackable marker may be attached to the fiducial body following the scanning and prior to positioning the instrument In some other embodiments, the trackable marker may be detached from the fiducial body prior to the scanning and reattached to the fiducial body prior to positioning the instrument.

The scanning the anatomical region with the formed appliance attached thereto may comprise MRI or CT scanning of the anatomical region with the formed appliance attached thereto. In some embodiments, the fiducial body may comprise aluminum or titanium. In such embodiments, scanning the anatomical region with the formed appliance attached thereto may comprise CT scanning of the anatomical region with the formed appliance attached thereto.

The anatomical region may be inside or in the vicinity of the skull of a patient, in which case the formed appliance should preferably mate with at least part of the surface of the nose and a part of the forehead.

The anatomical region may be the lower or upper human jaw of a patient, in which case the fiducial body should preferably be inserted between the inner surface of a lip and the nearby gingiva to maximize the portion of the fiducial body included in the scanned image of the jaw. This may also minimize patient discomfort.

The intermediate appliance may be removed from the face before being hardened to retain the appliance geometry to provide the formed appliance. This may increase patient comfort.

In some embodiments, the mouldable appliance may comprise a thermoplastic sheet. In such embodiments, pressing the mouldable appliance against the anatomical region or a model of the anatomical region to shape the mouldable appliance to conform to the surface geometry of the anatomical region to provide the intermediate appliance may comprise heating the mouldable appliance to render it soft and malleable and then pressing the thermoplastic sheet against the anatomical region or the model of the anatomical region.

In some other embodiments, the mouldable appliance may comprise a thermoplastic sheet with a lattice of metal wires embedded in the thermoplastic sheet to help retain its precise shape during the hardening process. In such embodiments, pressing the mouldable appliance against the anatomical region or a model of the anatomical region to shape the mouldable appliance to conform to the surface geometry of the anatomical region to provide the intermediate appliance may comprise pressing the mouldable appliance against the anatomical region or the model of the anatomical region, the lattice of metal wires being sufficiently soft and ductile to be plastically mouldable to the appliance geometry without injuring or causing pain to the anatomical region or injuring the facsimile of the anatomical region.

In yet some other embodiments, the mouldable appliance may comprise a bag defining an interior volume with a plurality of hard particles contained in the interior volume of the bag, and wherein the intermediate appliance may be hardened to retain the surface geometry of the anatomical region to provide the formed appliance by creating a partial vacuum within the interior volume of the sheet.

Attaching the formed appliance with the fiducial body attached thereto to the anatomical region may precede attaching the at least one trackable marker to the fiducial body.

After operating the tracking apparatus to determine the pose of the trackable marker attached to the fiducial body attached to the anatomical region, the method may further comprise detaching the at least one trackable marker from the fiducial body and re-attaching the at least one trackable marker to a different fiducial body, the different fiducial body being attached to a different formed appliance having a different appliance geometry shaped to mate with a different surface geometry of at least a portion of a different anatomical region. This allows reuse of the trackable marker, providing better operational economy.

In some embodiments, the anatomical region may comprise a human jaw. In such embodiments, pressing a mouldable appliance against the anatomical region or a model of the anatomical region to shape the mouldable appliance to conform to a surface geometry of the anatomical region to provide an intermediate appliance may comprise placing a mouldable appliance around the human teeth or a model of the human teeth to conform to the surface geometry of the human teeth to provide an intermediate appliance. In such embodiments, hardening the intermediate appliance to retain the appliance geometry shaped to mate with the surface geometry of the anatomical region to provide the formed appliance may comprise hardening the intermediate appliance to retain the appliance geometry shaped to mate with the surface geometry of the human teeth to provide the formed appliance.

In some embodiments, the fiducial body may have a plurality of symmetrical orientations. In such embodiments, aligning the segmented fiducial body region with a reference model of the fiducial body may comprise obtaining an approximate orientation of the anatomical region in the three-dimensional volume representation, for example as stored in the image header by the scanner or as calculated from the volumetric image content, and selecting one of the symmetrical orientations based on the approximate orientation. In such embodiments, providing a fiducial body attached to the formed appliance may comprise attaching the fiducial body to the formed appliance at a known direction of placement relative to the formed appliance and the anatomical region In some other embodiments, the fiducial body may be asymmetrical such that any one orientation of the fiducial body may be distinguishable from any other orientation of the fiducial body due to the asymmetry.

The method may further comprise operating a tracking apparatus and a data processor to dynamically calculate a spatial mapping between the coordinate frame of the fiducial body and the coordinate frame of an instrument located near the anatomical region, then mapping a location in the anatomical region referenced by the instrument to the three-dimensional volume representation of the at least a part of the fiducial body based on the mapping transformation resulting from the registration process. The measurement of the spatial mapping between the instrument and the fiducial body may be carried out using an electromagnetic, optical or ultrasonic pose sensor.

The method may further comprise providing at least one trackable marker, wherein the at least one trackable marker is attached to the fiducial body and wherein a spatial relationship of the at least one trackable marker to the fiducial body is known. The spatial relationship of the at least one trackable marker to the fiducial body is used in calculating the spatial mapping between the coordinate frames of the fiducial body and the instrument.

Providing a fiducial body attached to the formed appliance such that the fiducial body is rigidly fixed to the formed appliance may comprise attaching the fiducial body to the formed appliance rigidly and strongly enough such that the deflection of any portion of the fiducial body relative to the formed appliance is less than 1 millimeter when a force of less than 2 Newtons is applied to the fiducial body.

In some embodiments, the anatomical region may comprise one of at least part of a bridge of a nose, at least part of a forehead of a human body. In such embodiments, pressing a mouldable appliance against the anatomical region or a model of the anatomical region to shape the mouldable appliance to conform to a surface geometry of the anatomical region to provide an intermediate appliance may comprise placing a mouldable appliance over the at least part of the bridge of the nose, the at least part of the forehead and pressing the mouldable appliance against the face to conform to the surface geometry of the face to provide an intermediate appliance. In such embodiments, hardening the intermediate appliance to retain an appliance geometry shaped to mate with the surface geometry of the anatomical region to provide the formed appliance may comprise hardening the intermediate appliance to retain the appliance geometry shaped to mate with the surface geometry of the face at one of the at least part of the bridge of the nose, the at least part of the forehead and the at least part of the temples of the face to provide the formed appliance.

In accordance with other embodiments described herein there is provided an apparatus for registering an anatomical region with a scanned image of the anatomical region, the apparatus comprising:

a mouldable appliance configured for moulding into a formed appliance having an appliance geometry shaped to mate with a surface geometry of at least a portion of the anatomical region, wherein the formed appliance resists deformation and when attached to the anatomical region, the formed appliance resists displacement relative to the anatomical region; and a fiducial body, the fiducial body being attached to the mouldable appliance and shaped such that an orientation of the fiducial body relative to the anatomical region is uniquely determinable, and wherein when the mouldable appliance is moulded into the formed appliance, the fiducial body is rigidly fixed to the formed appliance such that the fiducial body is in a fixed spatial relationship with the formed appliance, wherein at least part of the fiducial body is detectable to a scanner conducting a scan of the anatomical region to provide a three-dimensional volume representation of the fiducial body in a scanned image.

The apparatus may further comprise at least one trackable marker, wherein the at least one trackable marker may be attachable to the fiducial body at an attachment location such that when the at least one trackable marker is attached to the fiducial body at the attachment location a spatial relationship of the at least one trackable marker to the fiducial body may be fixed.

The at least one trackable marker may be configured to be detachable from the fiducial body and re-attachable to a different fiducial body.

The fiducial body may comprise a scan detectable material for enabling the at least part of the fiducial body to be detectable by the scanner conducting a scan such that upon scanning the anatomical region with the formed appliance attached thereto and the fiducial body attached to the formed appliance to provide the scanned image, the interior of the anatomical region underlying the formed appliance may be distinguishable from the fiducial body in the scanned image.

The fiducial body may comprise a sealed hydrogel layer for enabling the fiducial body to be detectable by the scanner conducting an MRI scan, such that upon scanning the anatomical region with the formed appliance attached thereto and fiducial body attached to the formed appliance to provide the scanned image, the interior of the anatomical region underlying the formed appliance may be distinguishable from the fiducial body in an MRI scanned image.

The fiducial body may comprise aluminum or titanium for enabling the fiducial body to be detectable by the scanner conducting a CT scan, such that upon scanning the anatomical region with the formed appliance attached thereto and fiducial body attached to the formed appliance to provide the scanned image, the interior of the anatomical region underlying the formed appliance may be distinguishable from the fiducial body in a CT scanned image.

The mouldable appliance may comprise a thermoplastic sheet, the thermoplastic sheet being configured to become soft and malleable upon heating to a transition temperature such that the thermoplastic sheet, when rendered soft and malleable by heating to the transition temperature, may be pressable against the anatomical region to obtain the appliance geometry without injuring or causing pain to the anatomical region when pressed against the anatomical region due either to a force of pressing or the heated thermoplastic sheet being at the transition temperature.

The mouldable appliance may comprise a thermoplastic sheet with a lattice of metal wires embedded in the thermoplastic sheet, the lattice of metal wires being sufficiently soft and ductile to help retain the shape of the sheet while it is still soft, and to avoid injuring or causing pain to the anatomical region when pressed against the anatomical region.

The mouldable appliance may comprise a bag defining an interior volume with a plurality of hard particles contained in the interior volume of the sheet and an outlet for withdrawing gas or fluid from the interior volume, the outlet being sealable to impede air from leaking back into the interior volume, the sheet being configured to harden into the appliance geometry when a partial vacuum is created within the interior volume of the bag by withdrawing the gas or fluid from the interior volume, and the outlet is sealed to impede air from leaking back into the interior volume.

The thermoplastic sheet may be formed of a PolyForm® material such that the thermoplastic sheet may be configured to become soft and malleable upon being heated to a transition temperature. In various embodiments, the transition temperature may be lower than 70 degrees Celsius. The PolyForm® material may be the kind sold by Sammons Patterson Rolyan (www.pattersonmedical.com).

The fiducial body may be configured to be asymmetrical in shape such that any one orientation of the fiducial body may be distinguishable from any other orientation of the fiducial body due to the asymmetry.

The fiducial body may be configured to have a plurality of symmetrical orientations such that one of the symmetric orientations may be uniquely distinguishable based on the spatial relationship between the fiducial body and the anatomical region.

The anatomical region may be a human jaw, and the shape of the fiducial body may be designed to comfortably fit between the gingiva and the lips.

The formed appliance may comprise elastic ear straps.

The mouldable appliance may comprise a region designed to be pressed against the nasion, and a portion of the sides, and a portion of the bottom of a human nose.

The fiducial body may become rigidly fixed to the formed appliance where the fiducial body may be configured to connect to the formed appliance rigidly enough and strongly enough such that a deflection of any portion of the fiducial body relative to the formed appliance may be less than 1 millimeter when a force of less than 2 Newtons is applied to the fiducial body.

The fiducial body may become rigidly fixed to the formed appliance where the fiducial body may be configured to connect to the formed appliance rigidly enough and strongly enough such that a deflection of any portion of the fiducial body relative to the formed appliance may be less than 0.5 millimeter when a force of less than 2 Newtons is applied to the fiducial body.

BRIEF DESCRIPTION OF THE DRAWINGS

Embodiments of the present invention will now be described in detail with reference to the drawing, in which:

FIG. 2, in flowchart, illustrates an example of how the mapping transformation illustrated in FIG. 1 may be used to track a pose of an anatomical region or a surgical instrument displaceable in a coordinate reference frame in the scanned image;

Figure 1:
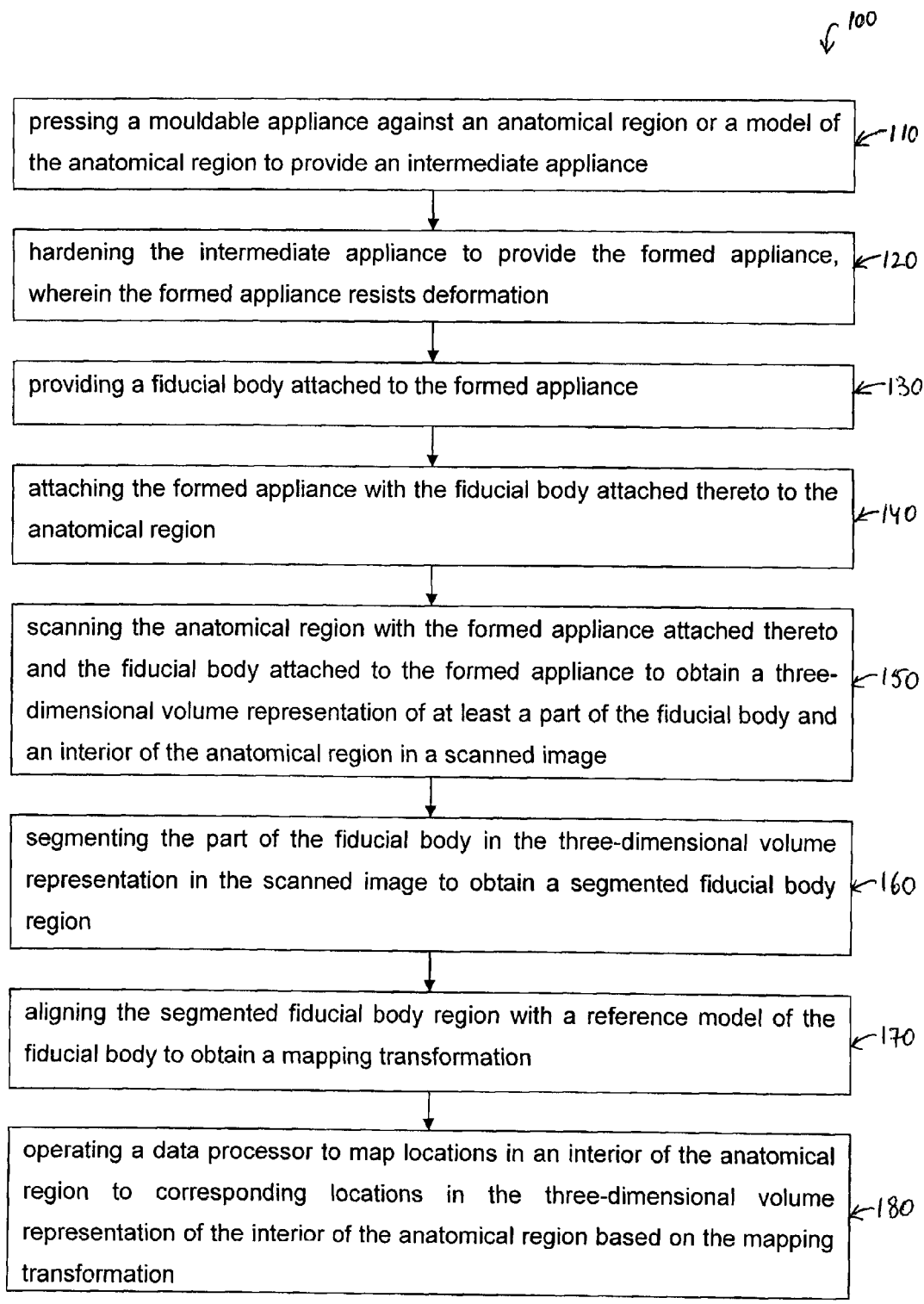
FIG. 1, in flowchart, illustrates an example of registering an anatomical region of a human body in a reference frame with a scanned image of the anatomical region.

The drawings, described below, are provided for purposes of illustration, and not of limitation, of the aspects and features of various examples of embodiments described herein. The drawings are not intended to limit the scope of the teachings in any way. For simplicity and clarity of illustration, elements shown in the figures have not necessarily been drawn to scale. The dimensions of some of the elements may be exaggerated relative to other elements for clarity. Further, where considered appropriate, reference numerals may be repeated among the figures to indicate corresponding or analogous elements.

DESCRIPTION OF EXEMPLARY EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing implementation of the various embodiments described herein.

The embodiments of the methods and apparatus described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example, a suitable programmable computers may be a server, network appliance, set-top box, embedded device, computer expansion module, personal computer, laptop, personal data assistant, mobile device or any other computing device capable of being configured to carry out the methods described herein. Program code is applied to input data to perform the functions described herein and to generate output information. The output information is applied to one or more output devices, in known fashion. In some embodiments, the communication interface may be a network communication interface. In embodiments in which elements of the invention are combined, the communication interface may be a software communication interface, such as those for inter-process communication (IPC). In still other embodiments, there may be a combination of communication interfaces implemented as hardware, software, and combination thereof.

Each program may be implemented in a high level procedural or object oriented programming or scripting language, or both, to communicate with a computer system. For example, a program may be written in XML, HTML 5, and so on. However, alternatively the programs may be implemented in assembly or machine language, if desired. The language may be a compiled or interpreted language. Each such computer program may be stored on a storage media or a device (e.g. ROM, magnetic disk, optical disc), readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the methods and apparatus of the described embodiments are capable of being distributed in a computer program product including a physical non-transitory computer readable medium that bears computer usable instructions for one or more processors. The medium may be provided in various forms, including one or more diskettes, compact disks, tapes, chips, magnetic and electronic storage media, and the like. The computer useable instructions may also be in various forms, including compiled and non-compiled code.

The method and apparatus described herein facilitate an automated registration of an object in a reference frame with a scanned image of the object. The object may be an anatomical region of a human body, such as for example, human face, teeth, skull, pelvis, etc.

Provided the anatomical region retains or regains its shape between the image scanning and the image-guided procedure, the method and apparatus described herein provide for continuous and accurate mapping between locations on or inside a human anatomical region, or locations on the anatomical region pointed to by a surgical instrument, during a surgical procedure and their corresponding three-dimensional volume representations in a scanned image. This accurate and continuous mapping facilitates tracking of a pose of an anatomical region or a surgical instrument displaceable in a coordinate reference frame. The term 'pose' generally refers to a position and orientation of the anatomical region or a surgical instrument. The instrument may be a pointer, an endoscope, a drilling bit, an implant, a scalpel, a collimated radiation beam collimator, or any type of apparatus that may reference a point in the anatomical region either by directly touching it or by aiming at it.

Reference is first made to FIG. 1, where an example of method 100 of registering an anatomical region of a human body in a reference frame with a scanned image of the anatomical region is provided. It will be appreciated that many of the steps of the method 100 may be performed in a different order from the order in which they are shown in the figures and from the order in which they are described below. For example, some steps may be performed before the step they are shown to proceed, and some method steps may be performed concurrently.

The various steps in the examples of the method 100 described below and shown in the Figures may be combined. For example, a new step described in relation to one example of the method 100 may be incorporated into a different example of the method 100 even if not explicitly stated.

In the example shown, the method 100 includes pressing 110 a mouldable appliance against the anatomical region or a model or a facsimile of the anatomical region to shape the mouldable appliance to conform to a surface geometry of the anatomical region to provide an intermediate appliance.

In some embodiments, the mouldable appliance may be a thermoplastic sheet configured to become soft and malleable upon heating to a transition temperature. The thermoplastic sheet, when rendered soft and malleable by heating to the transition temperature, is pressable against the anatomical region to obtain the appliance geometry such that when pressed against the anatomical region, there is no injury to the anatomical region either due to the force required to press the thermoplastic sheet against the anatomical region for the thermoplastic sheet to obtain the appliance geometry, or because of the temperature to which the thermoplastic sheet is required to be heated, or the transition temperature, before it becomes soft and malleable.

The thermoplastic sheet may be formed of PolyForm® material, or other low temperature thermoplastics used in splinting or immobilizing patients, such that the thermoplastic sheet is configured to become soft and malleable upon being heated to the transition temperature. In various embodiments, the transition temperature may be lower than 70 degrees Celsius. This may make the use of the heated thermoplastic sheet, heated to make it soft and malleable, safe and convenient for use on patients.

In various embodiments, a lattice of metal wires may be embedded in the sheet, allowing it to retain its moulded shape during the hardening process even when it is not in contact with the skin. In addition, it may, in some embodiments, shorten the time the thermoplastic sheet needs to remain in contact with the patient's skin. The metal wires should be sufficiently soft, ductile and plastically mouldable such that upon being pressed against the anatomical region or a facsimile of the anatomical region, the thermoplastic sheet may conform to the surface geometry of the anatomical region without injuring or causing pain to the anatomical region or damaging the facsimile of the anatomical region. Plasticity may be defined as a tendency of a material to undergo permanent deformation or non-reversible change of shape in response to applied forces. In various embodiments, the lattice may include electrical soldering wires.

In yet some other embodiments, the mouldable appliance may be a sheet or a bag defining an interior volume with a plurality of hard particles contained in the interior volume of the sheet and an outlet for withdrawing gas or fluid from the interior volume. In various embodiments, the bag or the sheet is made of an air-tight material. The outlet may be sealable to impede air from leaking back into the interior volume. The bag may be coupled to a vacuum pump configured to withdraw gas or fluid from the interior volume to create a partial vacuum in the sheet. By withdrawing gas or fluid from the interior volume of the sheet and sealing the outlet to impede air from leaking back into the interior volume, the sheet may be shaped to conform to the surface geometry of the anatomical region.

In the example shown, the method 100 includes hardening 120 the intermediate appliance to retain an appliance geometry shaped to mate with the surface geometry of the anatomical region to provide the formed appliance.

In some embodiments, the intermediate mask hardens into a formed mask simply by removing the intermediate mask from the anatomical region or the facsimile of the anatomical region and letting it cool down for a few minutes. In some other embodiments, the intermediate mask may harden into a formed mask while remaining attached to the anatomical region or the facsimile of the anatomical region.

The intermediate appliance can be hardened to provide the formed appliance so that once hardened, the formed appliance retains the appliance geometry shaped to mate with the surface geometry of the anatomical region and resists further deformation.

In the example shown, the method 100 includes providing 130 a fiducial body attached to the formed appliance. The fiducial body may be provided such that it is rigidly fixed to the formed appliance and is configured to be scannable to provide a three-dimensional volume representation of the fiducial body distinguishable from a three-dimensional volume representation of the anatomical region. Furthermore, the fiducial body may be provided such that the orientation of the fiducial body relative to the anatomical region is uniquely determinable based at least in part on a degree of asymmetry of the fiducial body.

In some embodiments, the fiducial body is attached to the mouldable appliance itself and when the mouldable appliance is moulded into the formed appliance, the fiducial body becomes rigidly fixed to the formed appliance. In some other embodiments, the fiducial body is attached to the formed appliance after the mouldable appliance is formed into a formed appliance. In some other embodiments, the fiducial body may also be attached to the intermediate appliance before it hardens into a formed appliance.

In some embodiments, providing a fiducial body attached to the formed appliance such that the fiducial body is rigidly fixed to the formed appliance comprises attaching the fiducial body to the formed appliance rigidly and strongly enough such that the deflection of any portion of the fiducial body relative to the formed appliance is less than 1 millimeter when a force of less than 2 Newtons is applied to the fiducial body. In some other embodiments, the fiducial body and the formed appliance are attached rigidly and strongly enough such that the deflection of any portion of the fiducial body relative to the formed appliance is less than 0.5 millimeter when a force of less than 2 Newtons is applied to the fiducial body. In yet some other embodiments, the fiducial body and the formed appliance may be attached such that the deflection of any portion of the fiducial body relative to the formed appliance is within a range of distance when a certain force is applied to the fiducial body. The specific displacement of the fiducial body relative to the formed appliance in response to the specific applied force are included herein as examples only and are not meant to be limiting.

In some embodiments, the fiducial body comprises a scan detectable material. The fiducial body may be entirely or partially composed of the scan detectable material. This may enable the fiducial body to be detectable in a scan in entirety or partially such that upon scanning the anatomical region with the formed appliance attached thereto and the fiducial body attached to the formed appliance to provide the scanned image, the interior of the anatomical region underlying the formed appliance is distinguishable from the fiducial body in the scanned image.

In some other embodiments, the fiducial body comprises a sealed hydrogel layer for enabling the fiducial body to be detectable by a scanner conducting an MRI scan by appearing brighter than its immediate surroundings, such that upon scanning the anatomical region with the formed appliance attached thereto and fiducial body attached to the formed appliance to provide the scanned image, the interior of the anatomical region underlying the formed appliance is distinguishable from the fiducial body in an MRI scanned image.

In some embodiments, the fiducial body may be made of or may include aluminum or titanium, or some other material which appears with a Hounsfield Units value range higher than 150 in a CT scan. The use of aluminum or titanium may enable the fiducial body to be detectable by a scanner conducting a CT scan, such that upon scanning the anatomical region with the formed appliance attached thereto and fiducial body attached to the formed appliance to provide a scanned image, the interior of the anatomical region underlying the formed appliance may be distinguishable from the fiducial body in a CT scanned image by showing with lower Hounsfield Unit values than the fiducial body.

The fiducial body may be provided attached to the formed appliance such that the orientation of the fiducial body may be uniquely determinable based at least in part on a degree of asymmetry of the fiducial body.

In some embodiments, the fiducial body may be non-rotationally symmetrical, i.e. the fiducial body may never look the same after any degree of rotation. This may allow to unambiguously distinguish the orientation of the fiducial body in the scanned image for the purpose of initializing the registration between the segmented fiducial body region in the image and the reference model of the fiducial body.

In some other embodiments, the fiducial body may have a plurality of rotationally symmetrical orientations, i.e. it may look the same after certain degrees of rotation. In such embodiments, the orientation of the fiducial body in the scanned image may be determined by using other features of the scanned image, such as, for example, orientation of the human body in the image as written the image header. For example, the fiducial body may be 180-degrees rotationally symmetric around its Z axis, such that it would appear the same whether its long axis is aligned with the X or the −X coordinate axis. In initializing the registration, the orientation in which the X direction is closer to a particular patient orientation in the image, for example, left may be selected, thereby removing the ambiguity. The general patient orientation within the image is typically available in the header of medical images stored in the standard DICOM image format.

In some other embodiments, the orientation of the fiducial body in the scanned image may be determined by placing the fiducial body relative to the anatomical region at a particular direction of placement, and then determining the unique and precise orientation of the fiducial body in the scanned image based on the particular direction of placement. For example, when the fiducial body is known to be placed in front of the skull, the skull may be segmented in the scanned image and its spatial relationship to the fiducial body may be used to select amongst alternative symmetrical orientations.

In yet some other embodiments, the fiducial body may be absolutely asymmetrical, i.e. under any rotation or change in orientation, the fiducial body, or a part thereof, may be distinguishable from any other rotation or change in orientation. In such embodiments, the unique and precise orientation of the fiducial body in the scanned image may be determined without the need to know any other information, such as the direction of placement of the fiducial body relative to the anatomical region. The shape of the fiducial body and how it is attached may be selected to facilitate determining the orientation of the fiducial body.

In some embodiments, a plurality of fiducial bodies may be used, where each fiducial body may be notionally one-dimensional or very small in volume, i.e. a point. In some other embodiments, a single three-dimensional fiducial body may be used. There may be some benefits associated with using a single (three-dimensional) fiducial body with an asymmetry or a non-rotational symmetry as opposed to a plurality of one-dimensional fiducial points. For example, first, the entire portion of the fiducial body need not be scanned as the pose, i.e. the position and orientation of the entire fiducial body may be determined by scanning only a portion of it. This may be advantageous as sometimes the scanner may miss a portion of the fiducial body. When multiple individual point markers are used and less than three appear in the scanned image, it may not be possible to determine the exact pose of the fiducial body in the image.

Second, accuracy and robustness may be improved over the plurality of one-dimensional fiducial points as surface-to-surface registration may be used if a single three-dimensional fiducial body is used. Generally, surface-to-surface registration is more tolerant of local segmentation errors due to noise and image artifacts. For example, in CT scans of teeth, fillings absorb nearly all X-ray photons and can cause severe streak artifacts in the CT image. As a result, a fiducial point that may fall into such streak may not be detected, or if detected may not be well localized, and may appear smeared. However, if a single three-dimensional fiducial body is used, it is usually sufficient that some portion of the surface would be identified for a correct and accurate result with a registration algorithm in which outliers (points too far out of alignment) may be identified and ignored.

Third, the fiducial body may be shaped in any way desired. For instance, the shape of the fiducial body may be determined by cost constraints, the shape of the formed appliance, the anatomical region being operated on etc. Ease of manufacturing and better ergonomics factors may also be relevant factors. In light of these factors, a single three-dimensional fiducial body may provide more flexibility and thus may be more suitable for different contexts.

In the example shown, the method 100 includes scanning 150 the anatomical region with the formed appliance attached thereto and the fiducial body attached to the formed appliance to obtain a three-dimensional volume representation of at least a part of the fiducial body and an interior of the anatomical region in a scanned image. In various embodiments, the scanning may be done using a CT or MRI scanner.

In the example shown, the method 100 includes segmenting 160 the part of the fiducial body in the three-dimensional volume representation of the at least a part of the fiducial body and the interior of the anatomical region in the scanned image to obtain a segmented fiducial body region.

Segmenting a fiducial body or a part of it may be defined as a way of separating a region depicting a fiducial body from the human anatomical region in a three-dimensional volume representation of the fiducial body and the interior of the human anatomical region. As an example, the segmented region of the fiducial body may be specified as a space-occupying volume marked on, for example, a 3D grid. As another example, the segmented region of the fiducial body may be specified as a surface, for example, in a form of a triangular mesh. The segmented region of the fiducial body may then be registered to a pre-stored model of the fiducial body to establish a coordinate relationship or a mapping transformation between the fiducial body and its three-dimensional volume representation in the scanned image. The pre-stored model of the fiducial body may be specified as, for example, either a volume or a surface, Other possible formats for describing the segmented region of the fiducial body and the model may include a collection of salient feature points and lines, medial-line representation, a combination of geometrical solid shapes, and others known in the art as being good descriptors of a space-occupying 3D shape. In various embodiments, the segmented region and the model may not have the same type of representation. Many methods are known for conversions between different representations, and thus, it may not be necessary for the segmented region and the model to have the same type of representation.

In some embodiments, the process of segmentation includes thresholding the scanned image at a level high enough to separate the fiducial body region from the surroundings. In some embodiments, the fiducial body is made of aluminum, and the thresholding process comprises thresholding the scanned image at a high range, for example 1400-2000 HU (Hounsfield units) for aluminum. The surroundings of the fiducial body in the scanned image may be low range regions requiring thresholding at 500 HU for CT scanned images. In some embodiments, the process of thresholding involves converting the scanned image in a binary format with each bit representation of the image containing a 1 or a 0, where a 1 represents a region of the image at or above the selected threshold level and a 0 representing otherwise.

In some embodiments, after thresholding, a list of all the connected regions in the binary image is prepared using a region growing algorithm. After a list of all the connected regions is prepared, the region with a volume and dimensions that best match the known volume and dimensions of the fiducial body, from the reference model statistics, is selected. The dimensions may include length, height, etc. of the fiducial body. In some other embodiments, segmenting of the fiducial body or a part thereof may be facilitated by separately segmenting the anatomical region in the three-dimensional volume representation of the at least a part of the fiducial body and the interior of the anatomical region. In some embodiments, the anatomical region may be segmented by selecting a thresholding range below 300HU. The regions embedded within the segmented anatomical region may be discarded, as the fiducial body is outside the anatomical region. In certain embodiments, where the relationship between the fiducial body and the anatomical region is known, the relationship may be used to further eliminate regions that are unlikely to represent the fiducial body even when they are not embedded in the anatomical region. For example, when the fiducial body is known to be in front of the head, all candidate regions at the back or sides of the segmented head may be discarded.

In the example shown, the method 100 includes aligning 170 the segmented fiducial body region with a reference model of the fiducial body to obtain a mapping transformation.

In some embodiments, aligning comprises computing a center of mass and axes of inertia of the segmented fiducial body region and aligning the segmented fiducial body region and a reference model of the fiducial body by aligning the center of mass and axes of inertia of the segmented fiducial body region with the center of mass and axes of inertia of the reference model. The statistics of the reference model of the fiducial body, such as the center of mass and axes of inertia, may be previously known from, for example, a design file. In some other embodiments, certain feature points (at least three) of the segmented may be detected and aligned with corresponding feature points in the reference model. The feature points may include sharp corners or tips of extrusions etc.

In various embodiments, the spatial descriptor of the reference model of the fiducial body may be recorded in a mechanical design file easily accessible by a data processor. In some other embodiments, the spatial descriptor of the reference model of the fiducial body may be measured from a manufactured sample of the fiducial body by scanning.

The statistics or description of the reference body for the registration can be stored in a plurality of different ways. In some embodiments, the reference body descriptor may be stored as a scanned image. In some other embodiments, the reference body descriptor may be stored as a surface description. In such embodiments, a surface-surface or surface-volume registration may be used. In yet some other embodiments, the reference body may be made of plastic with small metal markers in the shape of balls, cylinders or rings embedded in it. In such embodiments, the reference body descriptor may include information about the metal markers and that information may be used for point-to-point registration. In other embodiments, the reference body descriptor may be stored as a collection of feature points and lines, suitable for registration to corresponding feature points and lines extracted from the segmented region in the image using iterative closest-point (ICP) registration algorithm or similar.

In various embodiments, aligning of the segmented fiducial body region with a reference model of the fiducial body to obtain a mapping transformation comprises operating a data processor to execute an algorithm for registration of volume-occupying regions. Such algorithm for registration of volume-occupying regions may include surface-to-surface, volume-to-volume, points-to-surface, points-to-volume, points-to-points, lines-to-surface, lines-to-lines or any other body-to-body registration algorithm. These various registration algorithms are well-known in the art (See, for example, "Handbook of Biomedical Image Analysis, Volume III: Registration Models", ISBN 0-306-48607-5).

In the example shown, the method 100 includes operating 180 a data processor to map locations in an interior of the anatomical region to corresponding locations in the three-dimensional volume representation of the interior of the anatomical region based on the mapping transformation.

After a mapping transformation is determined, the locations of the anatomical region are mapped to the three-dimensional volume representation of the interior of the anatomical region based on the mapping transformation.

Reference is now made to FIG. 2, which shows as example of how the mapping transformation of method 100 can be used to track a pose of an anatomical region or a surgical instrument displaceable in a coordinate reference frame in the scanned image. The term 'pose' generally refers to a position and orientation of the anatomical region or the surgical instrument. The method below is discussed in context of tracking a pose of the anatomical region.

In the example shown, the method 200 includes providing 210 at least one trackable marker, wherein the at least one trackable marker is attached to the fiducial body and wherein a spatial relationship of the at least one trackable marker to the fiducial body is known.

In some embodiments, the trackable marker may be attached to the fiducial body even during the scanning in the registration process of method 100. In some other embodiments, the trackable markers may be attached after the scanning in the registration process of method 100.

In some embodiments, the trackable markers may be attached to the fiducial body prior to the fiducial body being attached to the formed appliance. In some other embodiments, the trackable markers may be attached to the fiducial body after the fiducial body is attached to the formed appliance.

In various embodiments, the fiducial body and the formed appliance may or may not be attached to the anatomical region before the trackable marker is attached to the fiducial body.

In some embodiments, providing the trackable marker may include detachably attaching the trackable marker to the fiducial body. The trackable marker may be detached from the fiducial body and re-attached to a different fiducial body, where the different fiducial body may be attached to a different formed appliance having a different appliance geometry shaped to mate with a different surface geometry of at least a portion of a different anatomical region.

In various embodiments, the trackable marker may be detached from the fiducial body prior to the scanning and reattached to the fiducial body prior to the positioning of the trackable marker on the fiducial body. In some other embodiments, the trackable marker may be attached to the fiducial body following the scanning and prior to positioning the instrument.

In various embodiments, the formed appliance may be separated from the anatomical region following the scanning and repositioned to mate with the anatomical region prior to positioning the trackable marker.

In various embodiments, the positioning of one or more trackable markers on the fiducial body is such that a spatial relationship between the reference frame of the fiducial body and the reference frame of the trackable markers is known. The spatial relationship between the reference frame of the fiducial body and the reference frame of the trackable markers may be known by measuring the spatial relationship on a production sample, by placing the markers at known feature points of the fiducial body, or directly from the design files when the fiducial body and the trackable markers configurations are co-designed. The spatial relationship of the one or more trackable markers and the fiducial body may be stored in a format accessible to the data processor.

In the example shown, the method 200 includes operating 220 a tracking apparatus to dynamically determine a pose of the at least one trackable marker. The tracking apparatus may be a stereoscopy optical sensor, such as ones sold by Claron Technology Inc. (Toronto, Ontario, Canada) or Northern Digital (Waterloo, Ontario, Canada), and the trackable marker may be an optically detectable marker. The optically detectable marker may be composed of a pattern of highly contrasting regions or retro-reflective spheres. The tracking apparatus may also be an electromagnetic pose sensor, such as one of the models sold by Ascension Technology Corporation (Burlington, Vt., USA).

In the example shown, the method 200 includes measuring 230 the pose of the fiducial body based on the pose of the at least one trackable marker. The pose of the fiducial body may be determined by using a known spatial relationship between the corresponding coordinate frame of the trackable markers and the corresponding coordinate frame of the fiducial body.

In various embodiments, once the pose of the fiducial body is measured, the mapping transformation of method 100 may be used to map the pose of the fiducial body, and therefore the pose of the anatomical region, to the three-dimensional volume representation of the at least a part of the fiducial body and the interior of the anatomical region.

Figure 3:
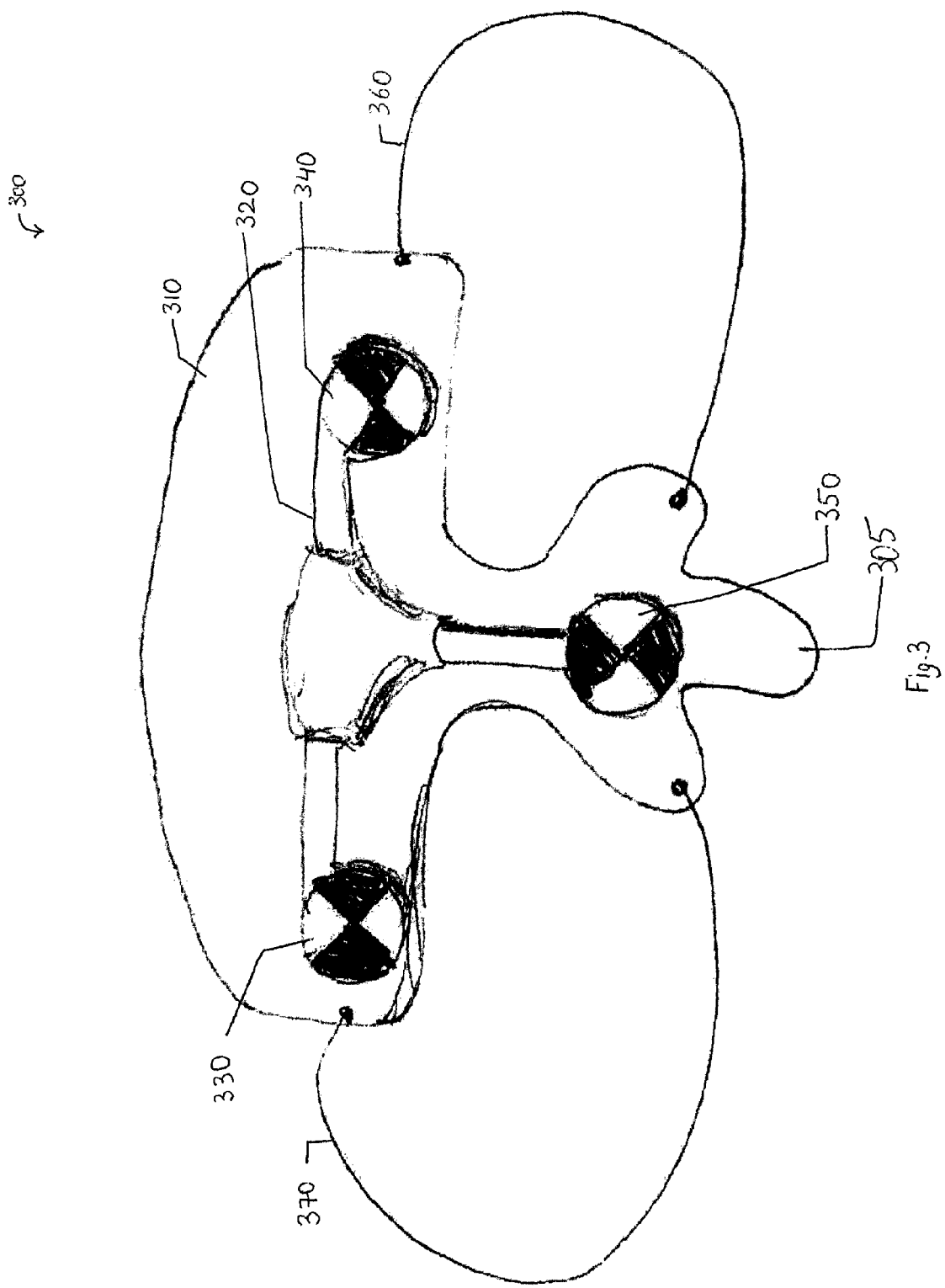
FIG. 3 illustrates an apparatus that may facilitate registration of an anatomical region of a human body in a reference frame with a scanned image of the anatomical region.

Reference is now made to FIG. 3, which shows an apparatus that may facilitate registration of an anatomical region of a human body in a reference frame with a scanned image of the anatomical region. An example of an anatomical region that the apparatus 300 may be used with may include any part of the human head. The apparatus may be configured to provide high registration accuracy for regions near the face, such as the nasal sinuses, the maxilla and the front of the brain. The registration accuracy may be very high with an error typically below 1 mm root-mean-square (RMS). The apparatus 300 comprises a mouldable appliance 310, a fiducial body 320, three trackable markers 330, 340 and 350. The apparatus may also include a right ear loop or strap 360 and a left ear loop or strap 370. The apparatus may also include a region 305 designed to be pressed against the nasion and a portion of the side and a portion of the bottom of a human nose. The combination of ear straps and contact with the nasion and all sides of the nose may provide a high rotational and lateral stability even when patient cooperation in placing apparatus 300 for maximum contact with the skin surface is hard or impossible to obtain.

The apparatus may be used to provide a reference unit that may be easily attached to and removed from a patient's anatomical region wherein the apparatus may be repeatedly reattached in exactly the same place with a high degree of accuracy.

The mouldable appliance 310 of apparatus 300 may be configured for moulding into a formed appliance having an appliance geometry shaped to mate with a surface geometry of at least a portion of the anatomical region. The mouldable appliance may be moulded into a formed appliance that resists deformation and when attached to the anatomical region, resists displacement relative to the anatomical region.

The mouldable appliance 310 may be a thermoplastic sheet configured to become soft and malleable upon heating to a transition temperature such that the thermoplastic sheet, when rendered soft and malleable by heating to the transition temperature, is pressable against the anatomical region to obtain the appliance geometry without injuring or causing pain to the anatomical region when pressed against the anatomical region due either to a force of pressing or the heated thermoplastic sheet being at the transition temperature.

In some embodiments, the mouldable appliance 310 optionally has a thickness of 1.5-2.5 mm. In some embodiments, the thermoplastic sheet may have a transition temperature of 60 to 65 degrees Celsius.

In some embodiments, the thermoplastic sheet may be made of polycaprolactone (PCL). In some other embodiments, the thermoplastic sheet may be made using Aquaplast ProDrape-T splinting material and may have a thickness of 1.6 mm or 2.4 mm. In yet some other embodiments, the thermoplastic sheet may be formed of a PolyForm® material such that the thermoplastic sheet may be configured to become soft and malleable upon being heated to the transition temperature.

In some other embodiments, the mouldable appliance 310 may consist of a thermoplastic sheet with a lattice of metal wires embedded in the thermoplastic sheet. The lattice of metal wires may be sufficiently soft and ductile to be plastically mouldable to the appliance geometry without injuring or causing pain to the anatomical region or damaging a facsimile of the anatomical region when pressed against the anatomical region or its model or facsimile. The thermoplastic sheet with the lattice of metal wires embedded in the thermoplastic sheet may be sufficiently soft and ductile to help retain the shape of the sheet while it is still soft. In various embodiments, the lattice may include electrical soldering wires. In some embodiments, the diameter of the electrical soldering wires may be 0.5-0.8 mm.

In some other embodiments, the mouldable appliance 310 may consist of a sheet or a bag defining an interior volume with a plurality of hard particles contained in the interior volume of the sheet and an outlet for withdrawing gas or fluid from the interior volume, the outlet being sealable to impede air from leaking back into the interior volume. In such embodiments, the sheet may be configured to harden into the appliance geometry when a partial vacuum is created within the interior volume of the sheet by withdrawing the gas or fluid from the interior volume, and the outlet is sealed to impede air from leaking back into the interior volume.

The fiducial body 320 attached to the mouldable appliance 310 is asymmetric, with the lengths of each of its three arms being unequal, thereby enabling for its orientation to be uniquely determinable. The fiducial body 320 may also be attached to the mouldable appliance 310 such that when the mouldable appliance is moulded into the formed appliance, the fiducial body 320 becomes rigidly fixed to the formed appliance such that the fiducial body 320 is in a fixed spatial relationship with the formed appliance. Furthermore, fiducial body 320 is made of aluminum and is thus easily separated from lower density surrounding regions in a CT scan of the anatomical region to provide a three-dimensional volume representation of the fiducial body 320 in a scanned image.

Fiducial body 320 may also be made of a hollow plastic body filled with a hydro-gel, causing it to appear similarly much brighter than its surrounding regions in an MRI scan, such that upon scanning the anatomical region with the formed appliance attached thereto and fiducial body 320 attached to the formed appliance to provide the scanned image, the interior of the anatomical region underlying the formed appliance is distinguishable from the fiducial body 320 in an MRI scanned image.

In some embodiments, the fiducial body 320 becomes rigidly fixed to the formed appliance either when attached to the formed appliance or when the mouldable appliance 310 is moulded into the formed appliance such that the fiducial body 320 is configured to connect to the formed appliance rigidly enough and strongly enough such that a deflection of any portion of the fiducial body 320 relative to the formed appliance is less than 1 millimeter when a force of less than 2 Newtons is applied to the fiducial body.

In some other embodiments, the fiducial body 320 becomes rigidly fixed to the formed appliance either when attached to the formed appliance or when the mouldable appliance 310 is moulded into the formed appliance such that the fiducial body 320 is configured to connect to the formed appliance rigidly enough and strongly enough such that a deflection of any portion of the fiducial body 320 relative to the formed appliance is less than 0.5 millimeter when a force of less than 2 Newtons is applied to the fiducial body.

In some other embodiments, the fiducial body 320 may be configured to have a plurality of symmetrical orientations such that any one orientation of the fiducial body is indistinguishable from at least one other orientation of the fiducial body due to the plurality of symmetrical orientations. In such embodiments, one of the symmetrical orientations may be uniquely distinguishable based on the spatial relationship between the fiducial body and the anatomical region. Furthermore, in such embodiments, aligning the segmented fiducial body region with a reference model of the fiducial body comprises obtaining an approximate orientation of the anatomical region in the three-dimensional volume representation of the anatomical region and selecting one of the symmetrical orientations of the fiducial body based on the approximate orientation.

In the apparatus 300, there are three trackable markers 330, 340 and 350 attached to the fiducial body 320. However, the number of trackable markers is exemplary only and should not be construed as limiting. In various embodiments, a minimum of three trackable locations may be needed for accurate pose measurement. Additional markers may be provided for increased accuracy and tracking robustness.

One or more trackable markers 330, 340 and 350 may be attachable to the fiducial body 320 at one or more attachment locations such that when at least one trackable marker 330, 340 and 350 is attached to the fiducial body 320 at the attachment location, a spatial relationship of the at least one trackable marker 330, 340 and 350 to the fiducial body 320 is fixed.

One or more trackable markers 330, 340 and 350 may be configured to be detachable from the fiducial body 320 and re-attachable to a different fiducial body.

The right ear loop 360 and the left ear loop 370 may be configured to be adjustable depending on the anatomical region and the patient or human to which it is attached. In some embodiments, the ear loops or straps 360 and 370 may be entirely elastic. In some other embodiments, the ear loops or straps 360 or 370 may only have a portion that is elastic.

In some embodiments, the apparatus 300 may be used where the anatomical region comprises one of at least part of a nose and at least part of a forehead of a human body.

The region 305 may be designed to be pressed against the human nose such that it covers a nasion, a portion of the side and a portion of the bottom of a human nose.

Figure 4:
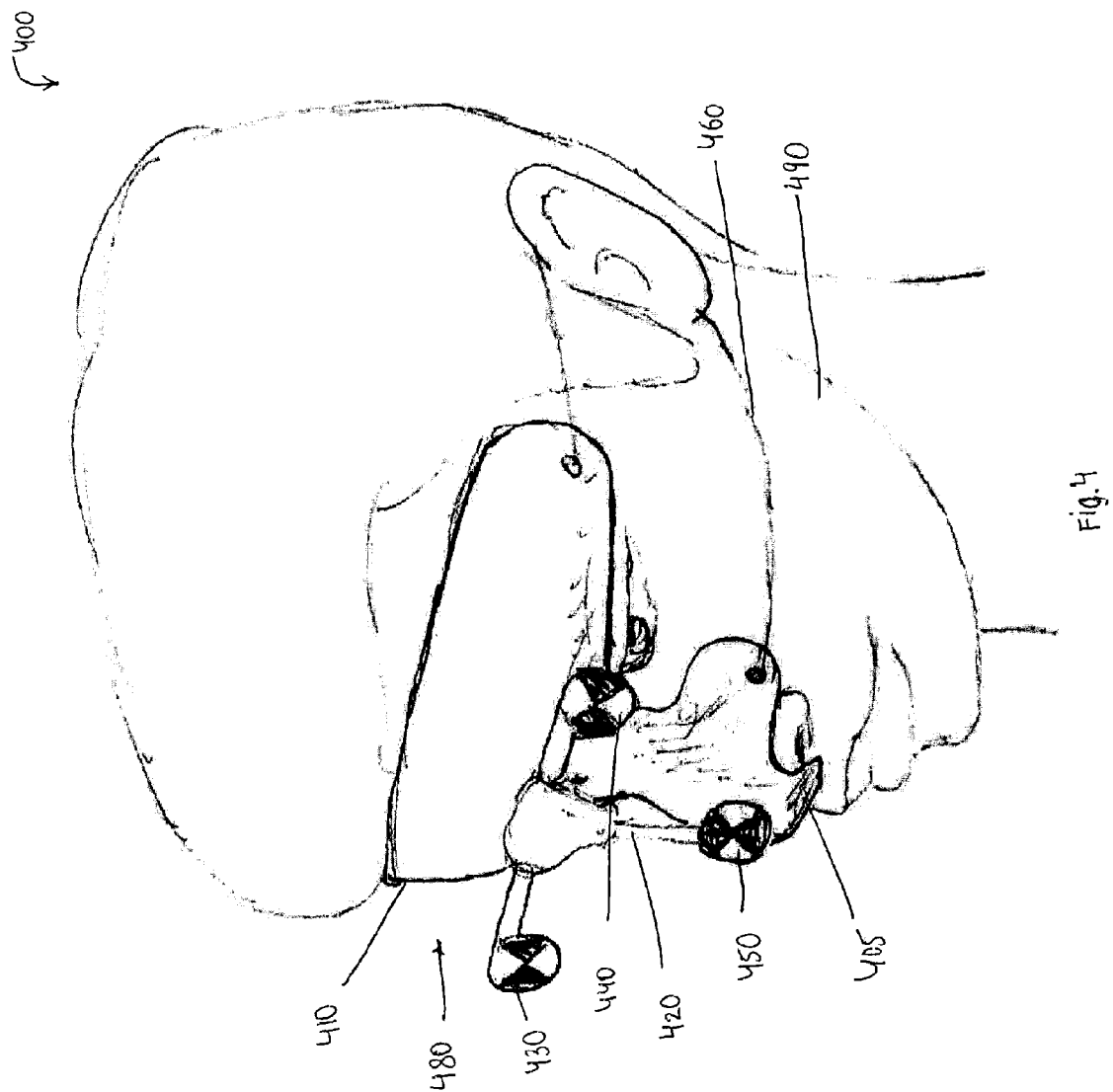
FIG. 4 illustrates an apparatus placed on a human face.

Reference is now made to FIG. 4, which shows the apparatus 480 placed on the human face 490. The apparatus 480, much like apparatus 300, comprises a formed appliance 410, a fiducial body 420, three trackable markers 430, 440 and 450, and a region 405 covering the nose. The apparatus 480 may also include a right ear loop 460 and a left ear loop (not shown).

In some embodiments, the apparatus 480 may be custom-made based on the profile and dimensions of the human face 490. The region 405 may also be customized based on average facial profile of population of a certain geographical area for which apparatus 480 is targeted. For example, in certain geographical areas, individuals may have smaller nose profile. For such populations, the region 405 may be small for a good fit with the human nose. In some embodiments, the apparatus 480 may not include the region 405. In such embodiments, there may or may not be some other region of the apparatus ensuring a good fit with a human anatomical region.

Reference is now made to FIGS. 5-10 illustrating the process of preparing a formed appliance from a mouldable appliance. The example discussed herein consists of a mask that may be used against a part of the human face.

Figure 5:
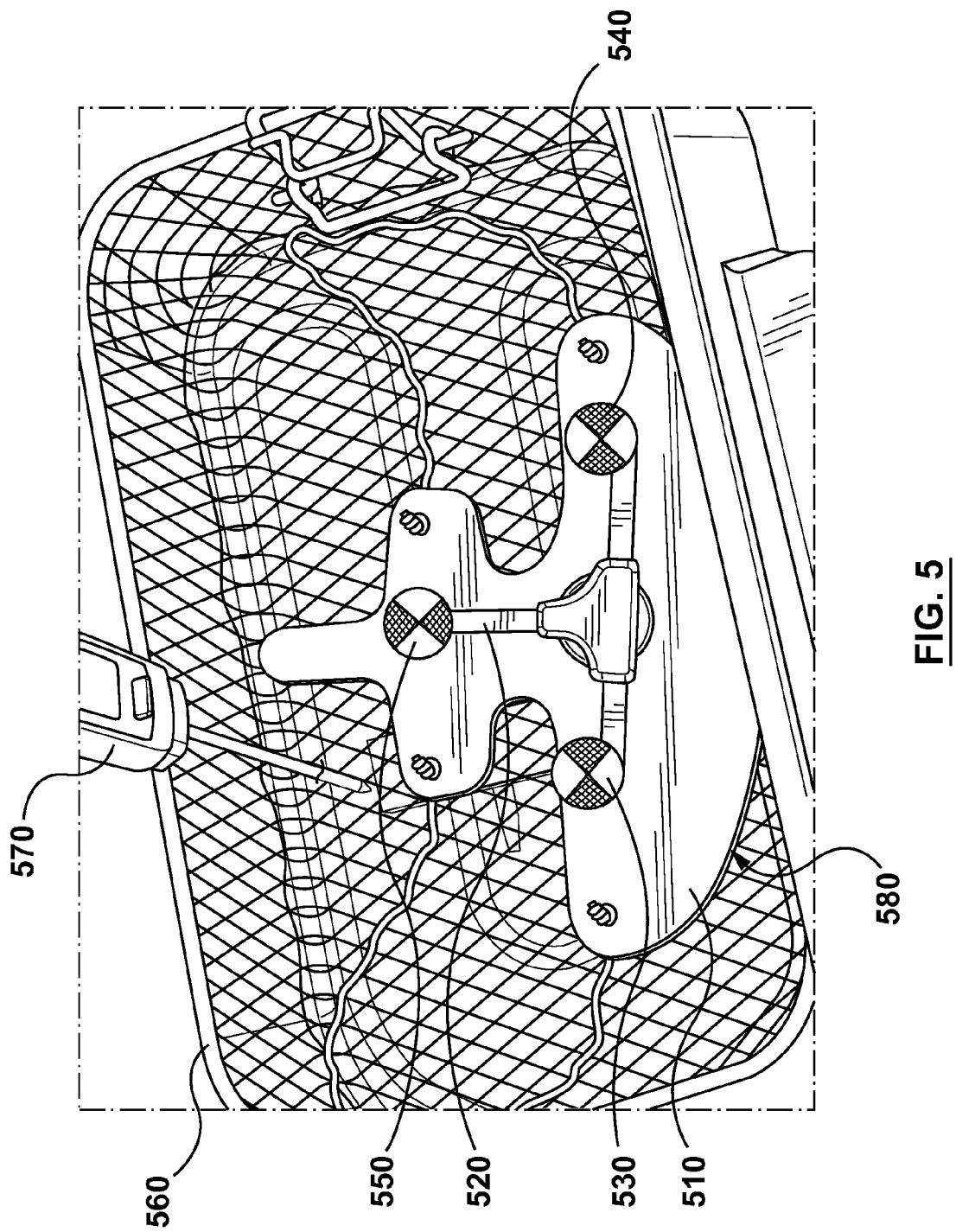
FIGS. 5-10 illustrate the process of preparing a formed appliance from a mouldable appliance.

FIG. 5 illustrates an apparatus 580 comprising a mouldable appliance 510 shaped in a form of a mask with a fiducial body 520 and three trackable markers 530, 540 and 550 attached thereto. The figure represents using a pan 560 to heat water to 65 degrees Celsius. A thermometer 570 may be used to measure the temperature of the water in the pan. Once the water is heated to 65 degrees Celsius, apparatus 580 is completely submerged in water, with the exception of the trackable markers 530, 540 and 550, for at least 20 seconds.

Figure 6:
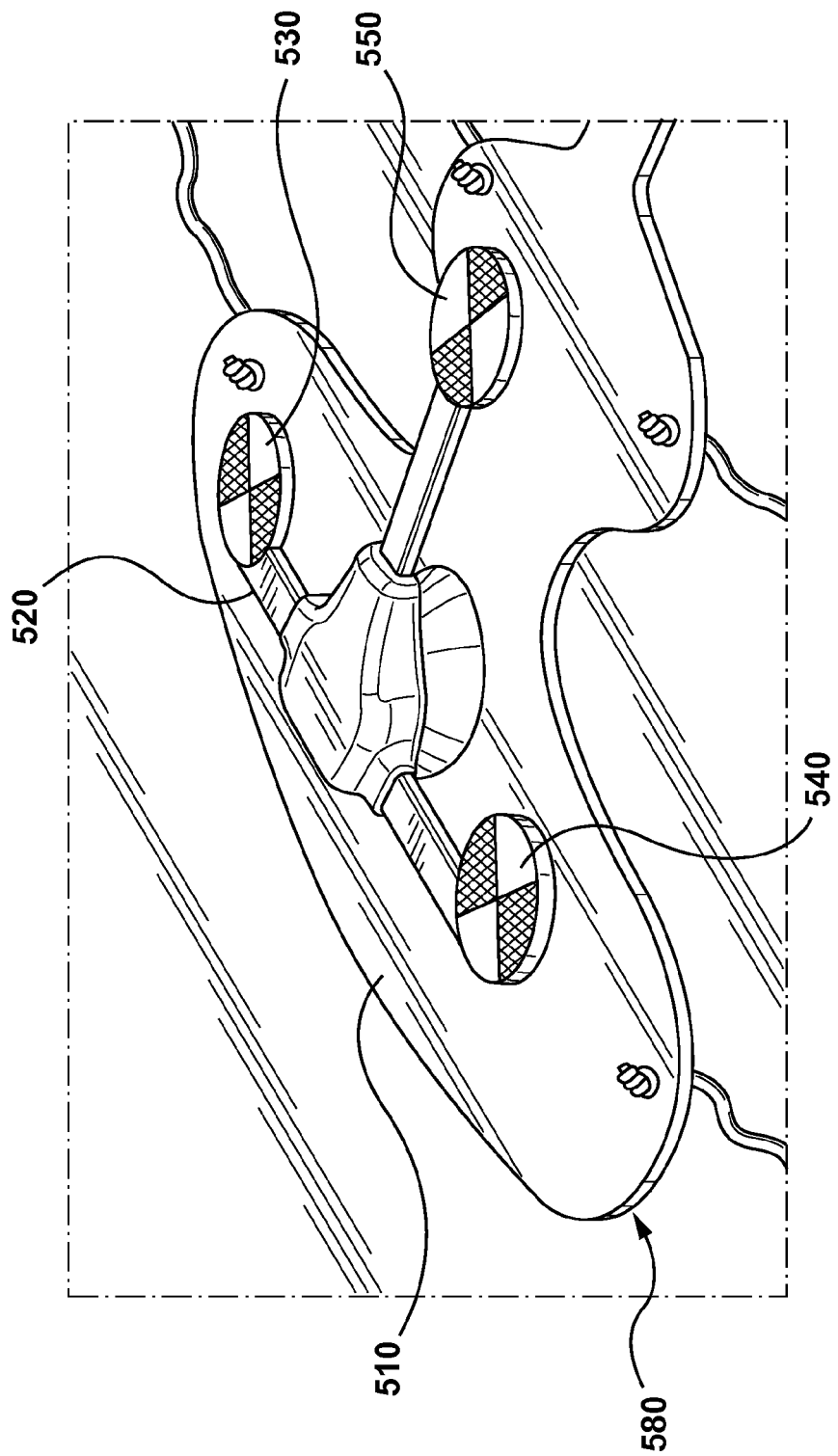

FIG. 6 illustrates removing the apparatus 580 from the pan 560 and placing it on a dry towel to remove excess water.

Figure 7:
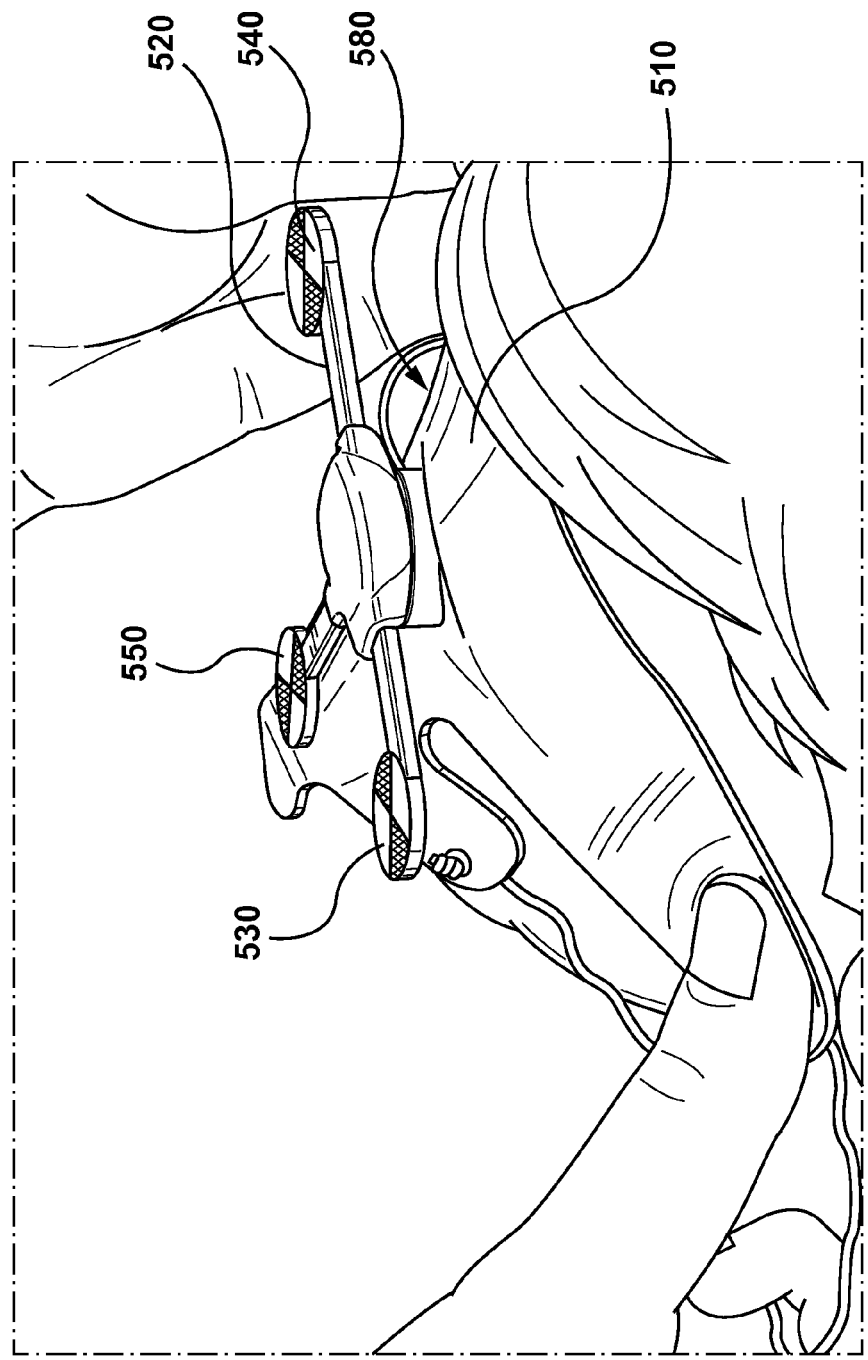

FIG. 7 illustrates placing the apparatus 580 on a patient's face. The patient's face is shown facing upwards and the apparatus 580 is placed to the face primarily covering the patient's forehead, the nose bridge and eyebrows.

Figure 8:
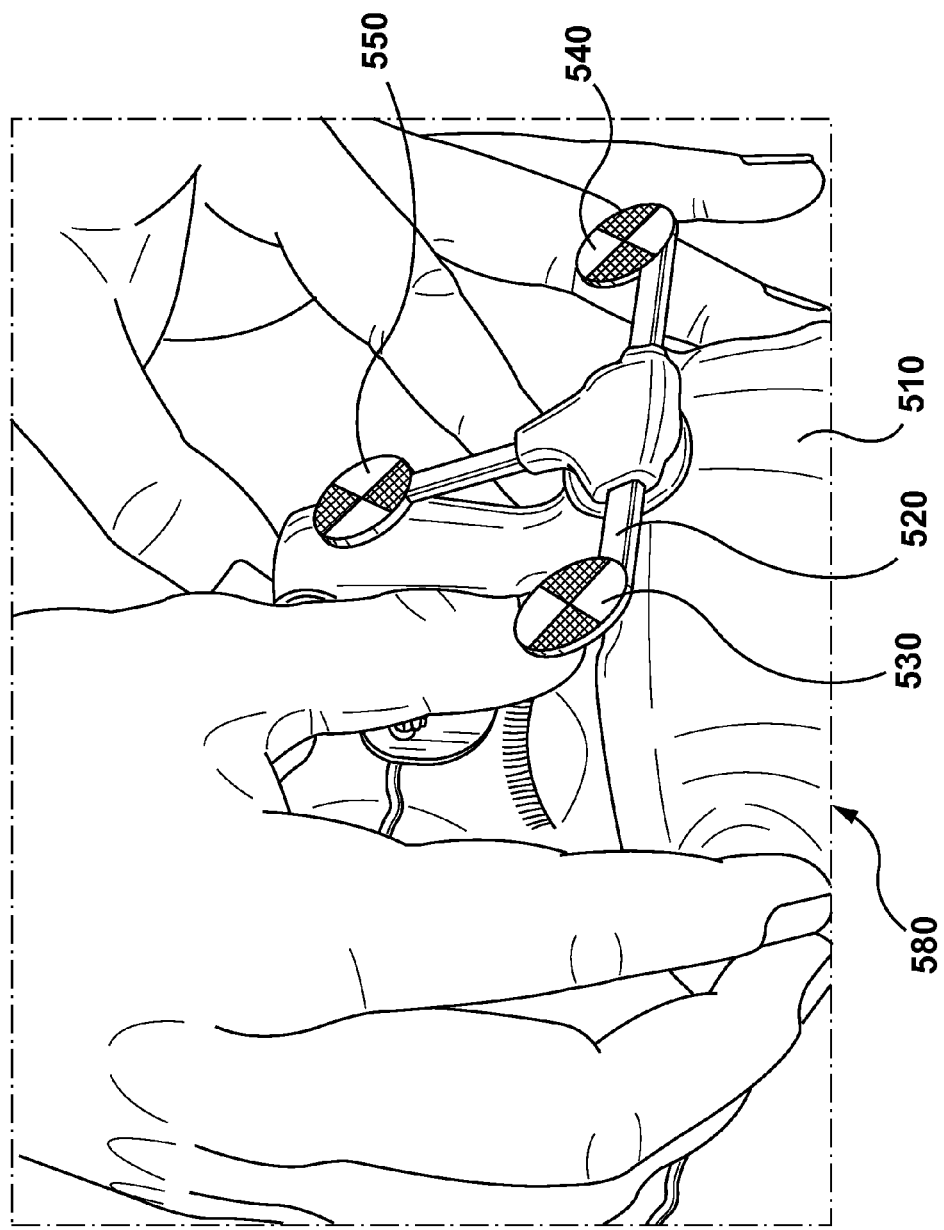

FIG. 8 illustrates conforming the apparatus 580 around the nose bridge, eyebrows, nostrils and the forehead. The apparatus 580 may be conformed to the part of the patient's face using human hands. The apparatus 580 may be conformed to the parts of the face for the duration of time that the apparatus 580 hasn't been hardened enough to preserve its shape. The duration of time may be 30 seconds.

Figure 9:
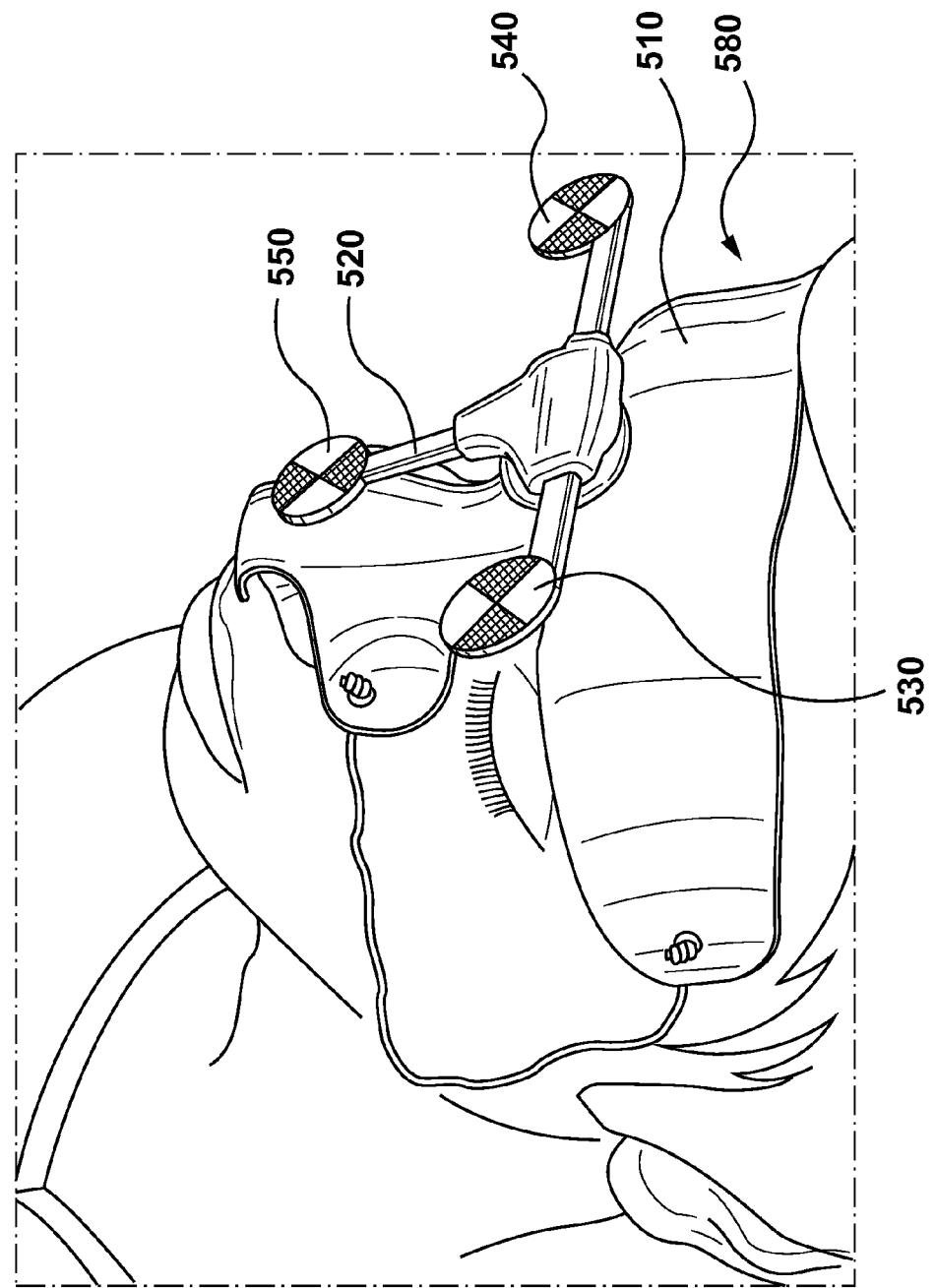

FIG. 9 illustrates leaving the conformed apparatus 580 on the patient's face before taking it off. The apparatus 580 may be left on the patient's face for another 30 seconds.

Figure 10:
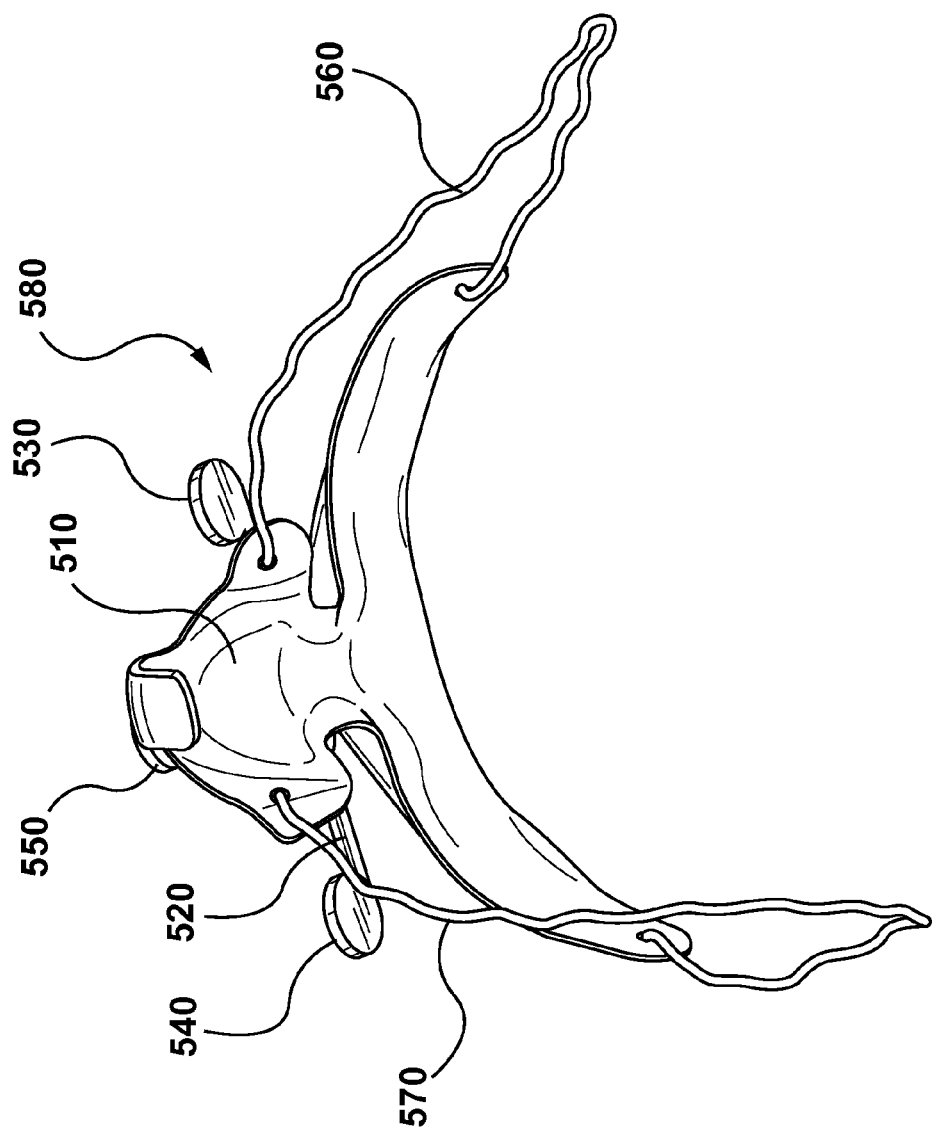

FIG. 10 illustrates removing the apparatus 580 from the face gently and allowing it to harden. The apparatus 580 may be allowed to harden for a minute or two. FIG. 10 also illustrates a right ear loop or strap 560 and a left ear loop or strap 570.

Reference is now made to FIGS. 11-14 illustrating placing of the formed appliance over an anatomical region. This is a crucial step before registration and before surgery. In these figures, the formed appliance is in a shape of a mask and the anatomical region is a patient's face.

Figure 11:
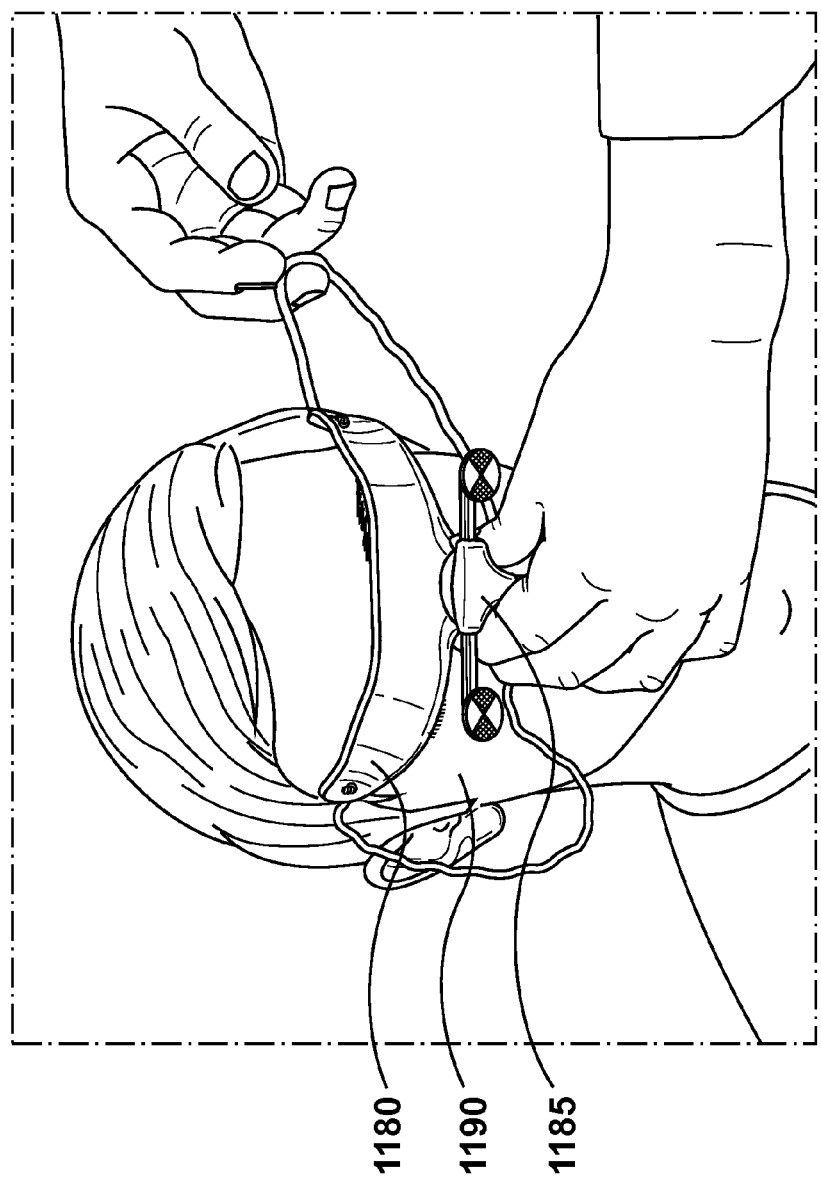
FIGS. 11-14 illustrate a process of placing a formed appliance over an anatomical region.

FIG. 11 illustrates bringing the formed appliance 1180 close to a patient's face 1190. The formed appliance 1180 may be placed on the face 1190 by placing the nose piece 1185 first and then slowing placing the formed appliance 1180 in the nose bridge and the forehead.

Figure 12:
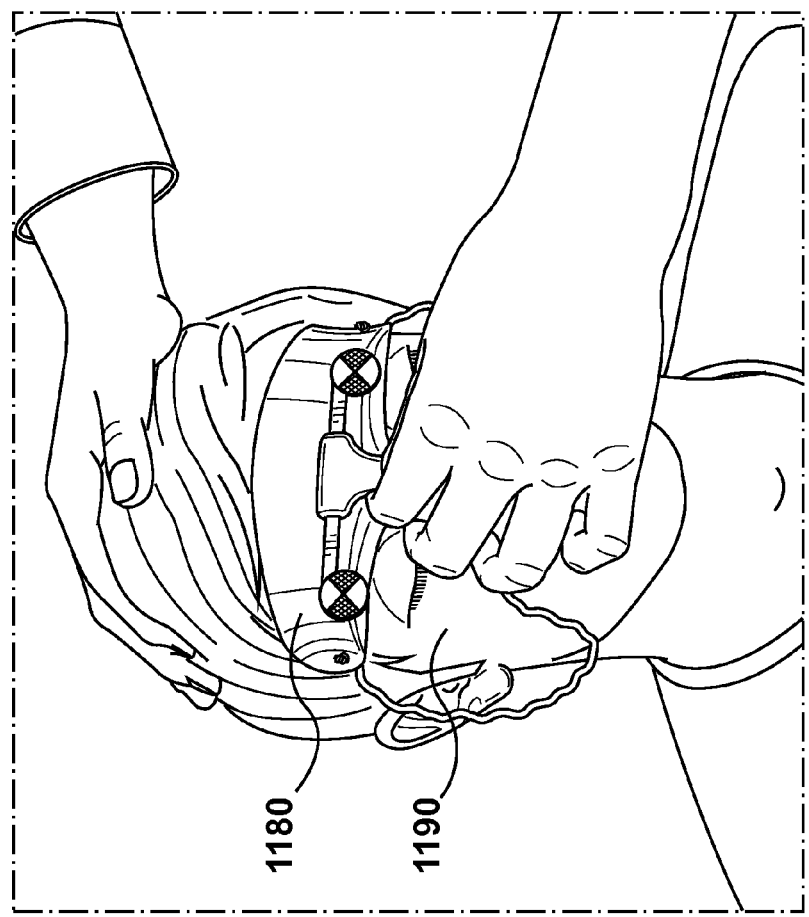

FIG. 12 illustrates holding the nose bridge area of the formed appliance 1180 or a trackable marker and gently pushing the formed appliance 1180 up or down, or right or left, or in a combination of directions to make sure that the formed appliance 1180 maximally conforms to the face 1190.

Figure 13:
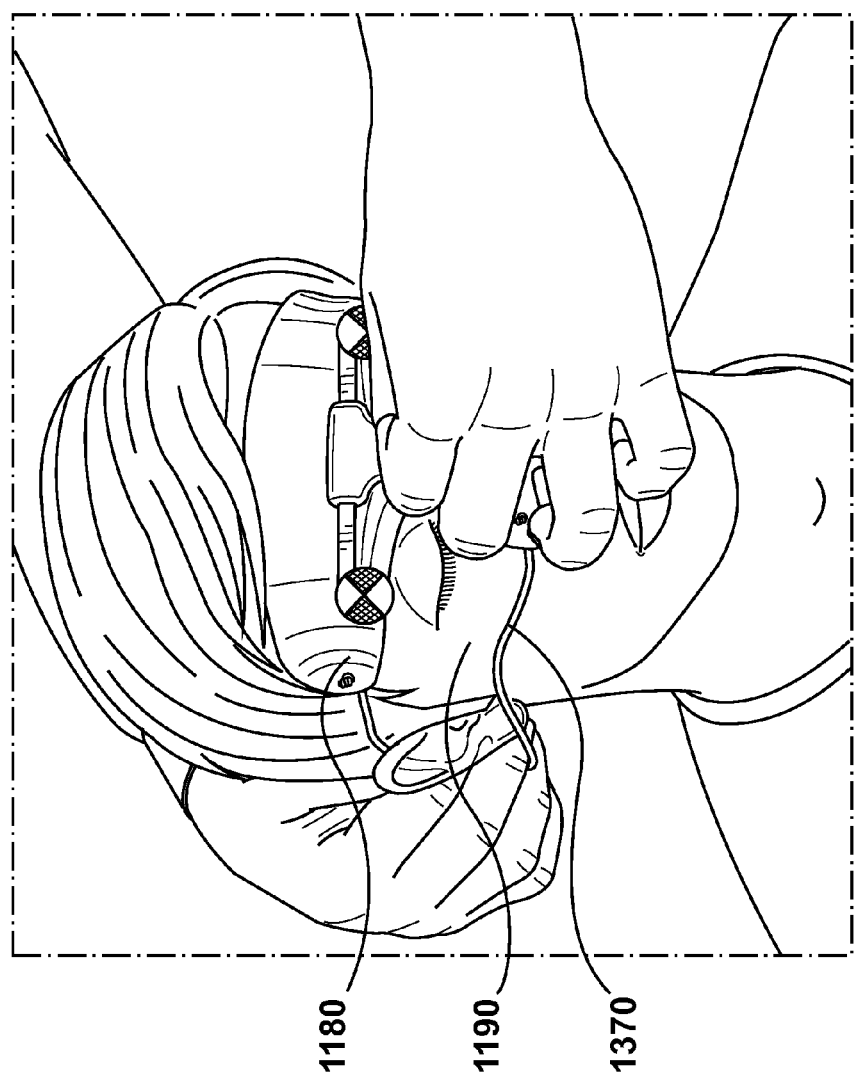

FIG. 13 illustrates holding the formed appliance 1180 and putting right ear loop (not shown) and left ear loop 1370 around the patient's right and left ear. The formed appliance 1180 may be held using human hands.

Figure 14:
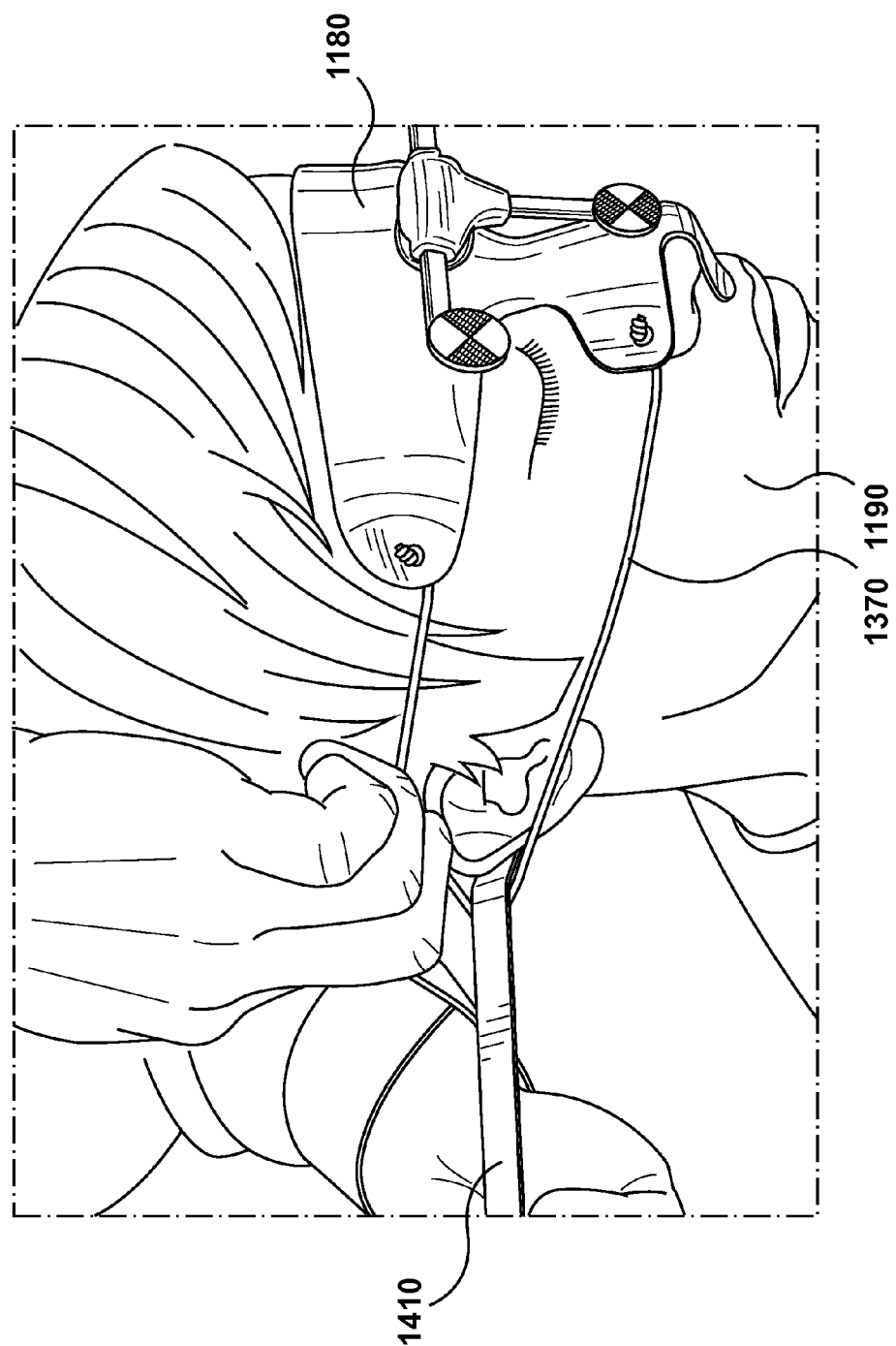

FIG. 14 illustrates a rare situation where one or both of the left ear loop 1370 and the right ear loop (not shown) don't provide sufficient support to the formed appliance 1180. FIG. 14 illustrates tightening the left ear loop 1370 and the right ear loop (not shown) to each other around the back of the patient's head. The left ear loop 1370 and the right ear loop (not shown) may be tightened to each other using a head band 1410.

In some embodiments, the anatomical region comprises a human jaw, and in such embodiments, the fiducial body is provided by inserting a part of the fiducial body between the lips and gingiva of a human mouth. In such embodiments, where the anatomical region comprises human jaw, pressing a mouldable appliance against the anatomical region or a model or facsimile of the anatomical region to shape the mouldable appliance to conform to a surface geometry of the anatomical region to provide an intermediate appliance comprises placing a mouldable appliance around the human teeth or a facsimile of the human teeth, such as a plaster or a stone cast, to conform to the surface geometry of the human teeth to provide an intermediate appliance. In such embodiments, hardening the intermediate appliance to retain the appliance geometry shaped to mate with the surface geometry of the anatomical region to provide the formed appliance comprises hardening the intermediate appliance to retain the appliance geometry shaped to mate with the surface geometry of the human teeth to provide the formed appliance.

Figure 15:
FIG. 15 illustrate an aluminum fiducial body attached to a facsimile of human teeth for dental applications.

Reference is now made to FIG. 15 illustrating aluminum fiducial body 1520 attached to a facsimile of human teeth 1590 for dental applications. In some embodiments, a thermoplastic sheet, to be formed into the formed appliance 1510, may be moulded over the teeth and/or gums of the patient or a plaster cast of the teeth and/or gums by pressing it against the teeth and/or the gums using finger pressure. In some other embodiments, when a plaster cast of the jaw is used, vacuum-forming of the thermoplastic sheet may be used.

FIG. 15 shows a fiducial body 1520 attached to a formed appliance 1510. The shape of the fiducial body 1520, in particular the apertures and design of the fiducial body 1520 may facilitate the determination of the orientation of the fiducial body in the scanned image of the anatomical region and the fiducial body during registration.

Figure 16:
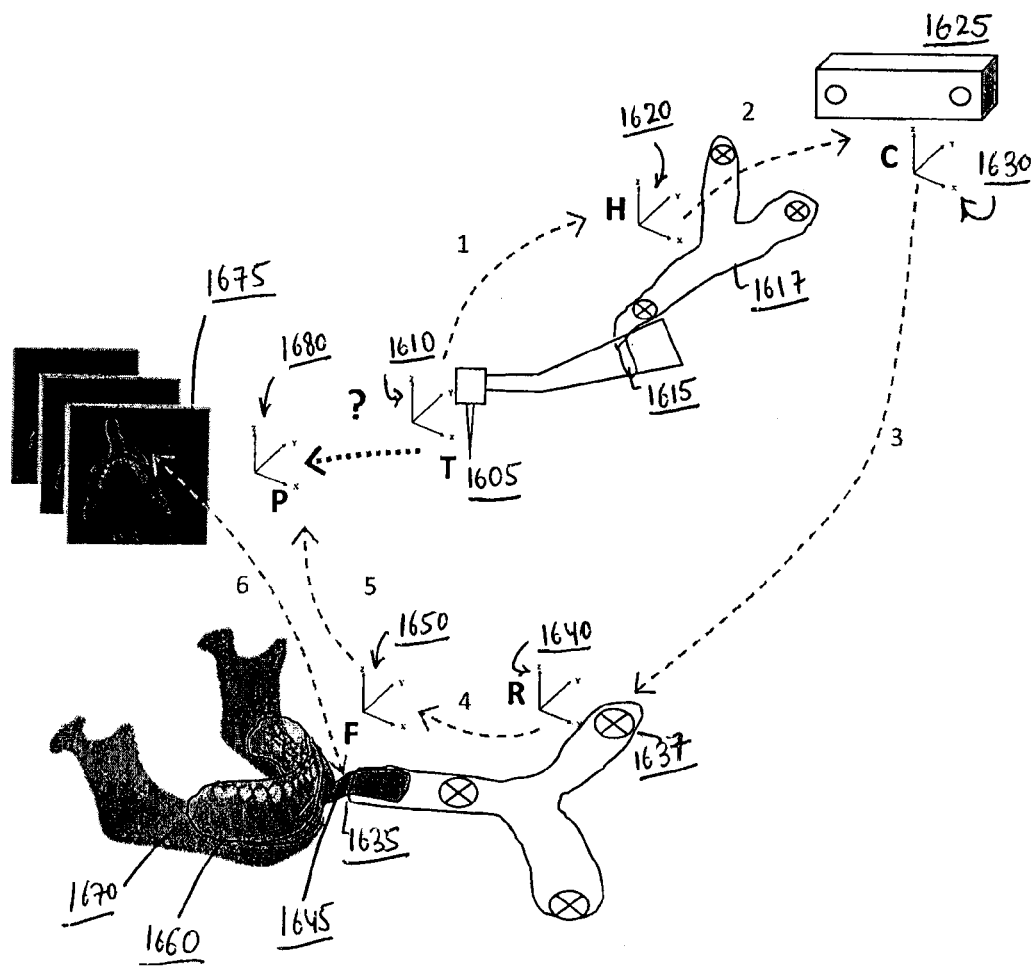
FIG. 16 illustrate a navigation system for dynamic mapping of an instrument to a scanned image of the anatomical region of the human body.

Reference is now made to FIG. 16 illustrating a navigation system 1600 for dynamic mapping of an instrument, such as a drill, to a scanned image of the anatomical region of the human body. FIG. 16 illustrates a tool tip 1605 with a corresponding coordinate system T 1610. A tool handle clamp 1615 mounts optically trackable tracker 1617 to the tool handle. Tracker 1617 has a corresponding coordinate system H 1620. Tracking camera 1625 has a corresponding coordinate system C 1630. Jaw reference tracker 1637, with a corresponding coordinate system R 1640, is trackable by camera 1625, and is detachably attached to fiducial body 1645 using clamp 1635. Fiducial body 1645, with a corresponding coordinate system F 1650, is moulded into a formed appliance 1660, which mates with an anatomical region of interest 1670, in this case human teeth or jaw. Three-dimensional volumetric image 1675, with a corresponding coordinate system P 1680, shows the interior of the anatomical region and the fiducial body. Trackers 1617 and 1637 are optically trackable by having at least three trackable target locations, shown as crosses in circles.

The tool tip 1605 may be a tip of any instrument that can reference a point in the anatomical region by directly touching it, pointing at it or aiming towards it. Examples of instruments may include a pointer, an endoscope, a drilling bit, a radiation beam etc.

The tool handle marker 1615 is attached to the tool handle to track the pose of the tool tip 1605.

The coordinate system F 1650 of the fiducial body 1645 is the same as the coordinate system of a reference model of the fiducial body as mentioned previously in method 100. Reference tracker 1637 is usually fixed, or detachably connected, to the fiducial body.

The three-dimensional volumetric image 1675 results from a scan of the anatomical region with the formed appliance attached thereto and the fiducial body attached to the formed appliance. The coordinate system P 1680 of the three-dimensional volumetric image 1675 is defined by the scanner during the scanning. The position of each image sample or voxel in the three-dimensional volumetric image 1675 is known using a mapper from image grid index to the coordinate system P 1680 of the three-dimensional volumetric image 1675 provided in, or may be computed from, for example, the information stored in the header of the image, as specified in the DICOM standard for medical image storage.

To operate, the navigation system 1600 can compute and constantly update the mapping from the tool tip 1605 with the coordinate system T 1610 to the three-dimensional volumetric image 1675 of the anatomical region of the patient with the coordinate system P 1680. This mapping may facilitate on the scanned image screen where the tool tip 1605 is in relationship to structures and target positions visible the pre-acquired three-dimensional volumetric image 1675. In order to accomplish this, a sequence of chained mappings is used:

$$T \xrightarrow{1} H \xrightarrow{2} C \xrightarrow{3} R \xrightarrow{4} F \xrightarrow{5} P$$

The mapping from T (tool tip coordinate system 1610) to H (tool handle marker coordinate system 1620) (shown as 1 in FIG. 16) may be obtained by using a special calibration tool in advance of the start of the surgical procedure. The special calibration tool may be a special jig. Such tool-tip calibration jigs are well known in the art.

The mapping from H (tool handle marker coordinate system 1620) to C (tracking camera coordinate system 1630) (shown as 2 in FIG. 16) is measured by the camera in real time.

The mapping from C (tracking camera coordinate system 1630) to R (reference tracker coordinate system 1640) (shown as 3 in FIG. 16) is also measured by the camera in real time.

Figure 17:
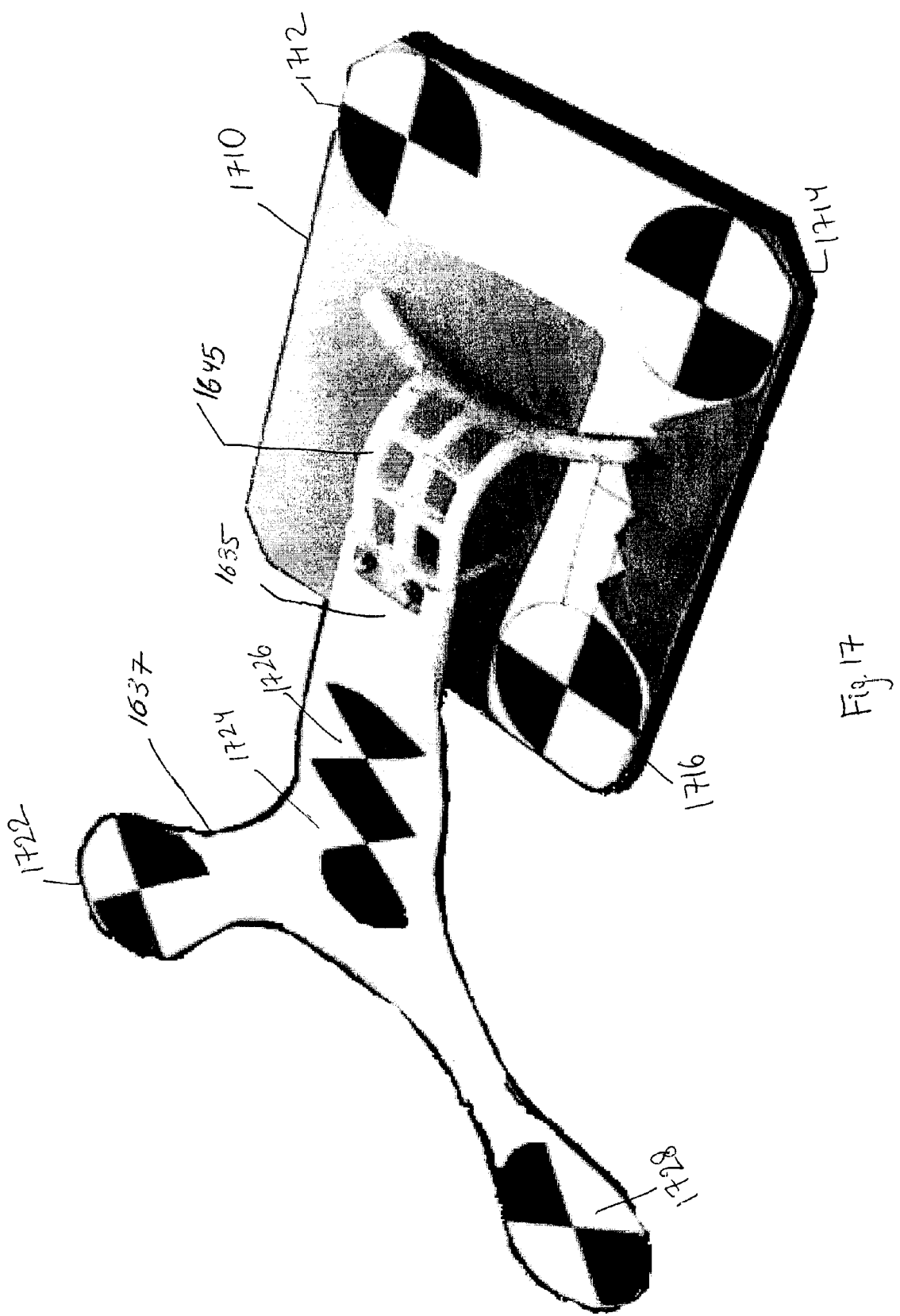
FIG. 17 illustrate a calibration fixture usable to determine a mapping from a reference coordinate of a trackable marker attached to a fiducial body and the reference coordinate of the fiducial body.

The mapping from R (reference tracker coordinate system 1640) to F (fiducial body coordinate system 1650) (shown as 4 in FIG. 16) may either be obtained from a design file, or experimentally calibrated using a special fixture during design or manufacturing, as shown in FIG. 17. This mapping may be saved in a file available to a data processor.

The mapping from F (fiducial body coordinate system 1650) to P (three-dimensional volumetric image coordinate system 1680) (shown as 5 in FIG. 16) is the output of the registration algorithm as discussed in FIG. 1 and method 100.

Reference is now made to FIG. 17 illustrating a way of determining a mapping from R (reference marker coordinate system 1640) to F (fiducial body coordinate system 1650) (shown as 4 in FIG. 16) using a calibration fixture 1710. The calibration fixture 1710 includes markings on it showing the origin and axes of the coordinate system F 1650 associated with the fiducial body 1645. This coordinate system F 1650, referred to as reference coordinate system, is the same as the coordinate system associated with the reference model of the fiducial body used in registration as discussed in FIG. 1 and method 100.

The calibration fixture 1710 is shown with a fiducial body 1645 mounted on it, where the fixture is designed for calibrating the mapping R (reference marker coordinate system 1640) to F (fiducial body coordinate system 1650). The calibration fixture 1710 is provided with three trackable markers or target locations 1712, 1714 and 1716. The fiducial body 1645 has a tracker 1637 attached using clamp 1635. Tracker 1637 carries four optically trackable markers 1722, 1724, 1726 and 1728 allowing it to be tracked by camera 1625. The process of calibration typically involves tracking the calibration fixture 1710 and the tracker 1637 on the fiducial body 1645 and operating a data processor to determine a mapping between the coordinate systems 1640 and 1650 of FIG. 16. Other types of tracking, such as, for example, electromagnetic, may also be carried out based on the choice of the trackable markers. The coordinate mapping between R (reference marker coordinate system 1640) and F (fiducial body coordinate system 1650) may then be stored in a file accessible by a data processor for later retrieval.

Figure 18:
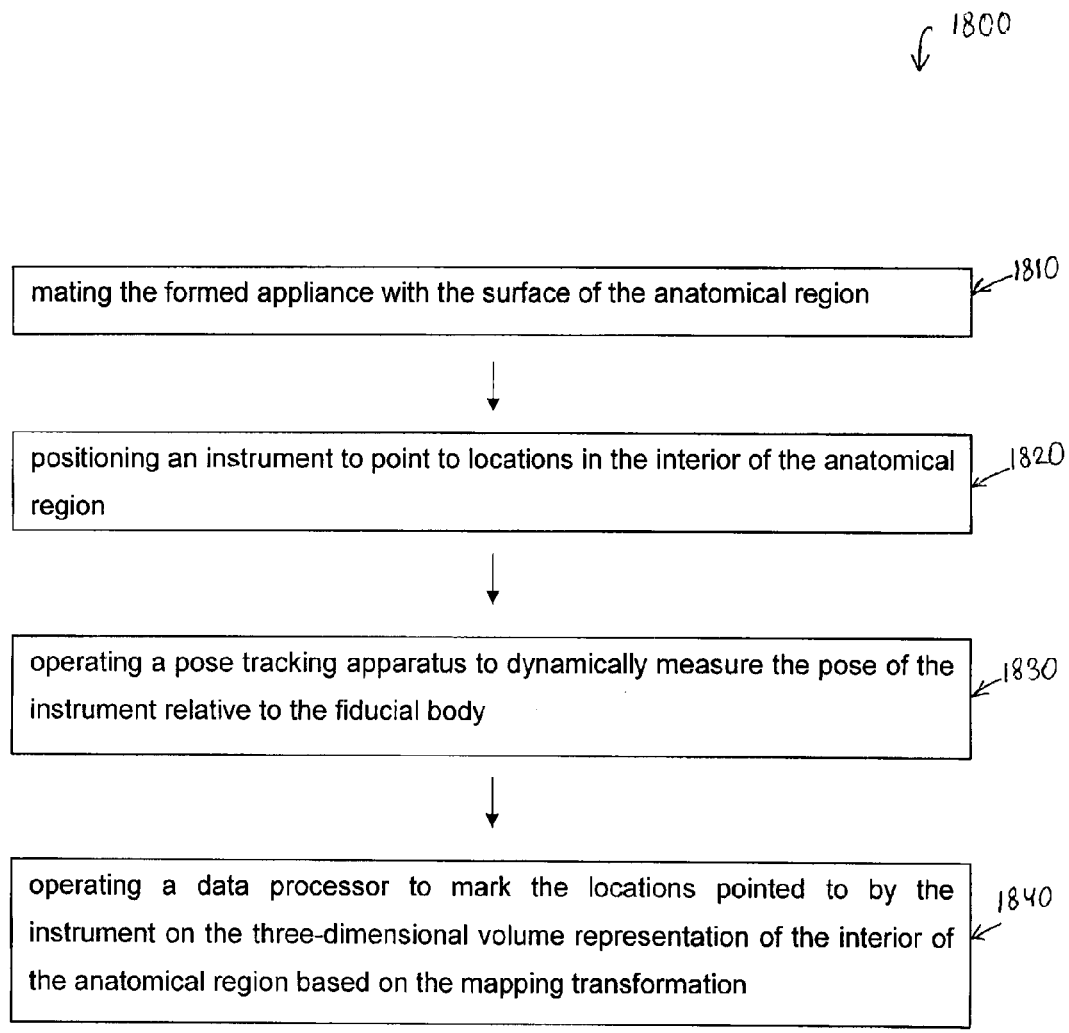
FIG. 18 illustrate a method for actively and dynamically mapping an instrument to a three-dimensional volumetric image of the anatomical region of a human body.

Reference is now made to FIG. 18, where an example of method 1800 for actively and dynamically mapping an instrument to the three-dimensional volumetric image of the anatomical region of a human body is provided.

In the example shown, the method 1800 may include an optional step of mating 1810 the formed appliance with the surface of the anatomical region or ensuring that the formed appliance is mated with the surface of the anatomical region. In various embodiments, the formed appliance is removed from the anatomical region after scanning during registration, and reattached to the anatomical region at a later day or time for the surgical procedure. In some other embodiments, the formed appliance is never removed from the anatomical region after the scanning during registration and continues to be placed on the anatomical region during the surgical procedure.

In the example shown, the method 1800 includes positioning 1820 an instrument to point to locations in the interior of the anatomical region. As mentioned before, an instrument may be anything that can reference a point in the anatomical region by directly touching it, pointing at it or aiming towards it. Examples of instruments include a pointer, an endoscope, a drilling bit, a radiation beam etc.

In the example shown, the method 1800 may include operating 1830 a pose tracking apparatus to dynamically determine a pose of the instrument relative to the fiducial body. The pose of the instrument may be measured by attaching a marker of some sort to the instrument and to the body serving as a reference frame, such as for example the fiducial body.

The marker may be an optically detectable marker, for example, in which case the tracking apparatus may be an optical sensor so that the tracking apparatus may be used to optically detect the pose and orientation of the trackable marker on the instrument. An electromagnetic tracking may also be used. As illustrated in FIG. 16, a series of transformations may be used to measure the pose of the instrument relative to the fiducial body. Referring back to FIG. 16, such transformations may include $^1H\rightarrow{}^2C\rightarrow{}^3R\rightarrow{}^4F$, where H represents a tool handle marker coordinate system 1620, C represents a tracking camera coordinate system 1630, R represents a reference marker coordinate system 1640 and F represents a fiducial body coordinate system 1650.

In the example shown, the method 1800 may include operating 1840 a data processor to mark the locations pointed to by the instrument on the three-dimensional volume representation of the interior of the anatomical region based on the mapping transformation. As illustrated in FIG. 16, a series of transformations may be used to mark the locations pointed to by the instrument on the three-dimensional volume representation of the interior of the anatomical region. Such transformations may include $^1H\rightarrow{}^2C\rightarrow{}^3R\rightarrow{}^4F\rightarrow{}^5P$.

The transformation from $^4F\rightarrow{}^5P$ (i.e. from F representing a fiducial body coordinate system 1650 to P representing a three-dimensional volumetric image coordinate system 1680, shown as 5 in FIG. 16) may be accomplished by using the mapping transformation determined by registration in method 100 of FIG. 1.

The various methods described herein may also be implemented as a system for registering an anatomical region with a scanned image of the anatomical region. The system may comprise a mouldable appliance, a fiducial body, a memory module and a data processor.

The mouldable appliance may be configured for moulding into a formed appliance having an appliance geometry shaped to mate with a surface geometry of at least a portion of the anatomical region, wherein the formed appliance resists deformation and when attached to the anatomical region, the formed appliance resists displacement relative to the anatomical region.

The fiducial body may be attached to the mouldable appliance and shaped such that an orientation of the fiducial body relative the anatomical region is uniquely determinable, and wherein when the mouldable appliance is moulded into the formed appliance, the fiducial body becomes rigidly fixed to the formed appliance such that the fiducial body is in a fixed spatial relationship with the formed appliance, wherein at least part of the fiducial body is detectable to a scanner conducting a scan of the anatomical region to provide a three-dimensional volume representation of the fiducial body in a scanned image.

The memory module may be configured to store statistics regarding a reference model of the fiducial body. The statistics regarding the reference model of the fiducial body may include surface or volume information about the reference model. The memory model may also be used to store a mapping transformation determined as a result of registration, where the mapping transformation represents a transformation between the anatomical region and the fiducial body, since the two have the same corresponding coordinate frames, and the three-dimensional volumetric representation of the interior of the anatomical region and the fiducial body.

The data processor may be configured to segment a part of the fiducial body in a three-dimensional volume representation of the at least a part of the fiducial body in a scanned image to obtain a segmented fiducial body region. The data processor may be further configured to align the segmented fiducial body region with the reference model. The data processor may also be configured to determine a mapping transformation between the anatomical region or the fiducial body and the three-dimensional volumetric representation of the interior of the anatomical region and the fiducial body.

The system may also include at least one trackable marker, wherein the at least one trackable marker is attachable to the fiducial body at an attachment location such that when the at least one trackable marker is attached to the fiducial body at the attachment location, a spatial relationship of the at least one trackable marker to the fiducial body is fixed.

The system may also include a receiving module configured to receive the known spatial relationship of the at least one trackable marker to the fiducial body when the at least one trackable marker is attached to the fiducial body. The memory module may be configured to store the known spatial relationship for later use.

The system may also include a pose tracking apparatus configured to determine a pose of the trackable marker attached to the fiducial body, wherein the fiducial body is rigidly fixed to the formed appliance, and wherein the formed appliance is attached to the anatomical region.

The data processor may be further configured to track a pose of an anatomical region displaceable in a coordinate reference frame and determine displacement of at least a portion of the anatomical region in the scanned image based on the pose of the trackable marker, the spatial relationship of the at least one trackable marker to the fiducial body and the mapping transformation between the fiducial body and the three-dimensional volumetric representation of the fiducial body and the interior of the anatomical region.

In some embodiments, the pose tracking apparatus may be further configured to dynamically measure a pose of an instrument pointing to locations in the interior of the anatomical region relative to the fiducial body. In such embodiments, the data processor may be further configured to mark the locations pointed to by the instrument on the three-dimensional volume representation of the interior of the anatomical region based on the mapping transformation.

The various methods described herein may also be implemented as a surgery product for registering an anatomical region with a scanned image of the anatomical region. The surgery product may comprise a computer readable storage medium having computer instructions stored thereon.

The computer instructions may configure a computer readable storage medium to store statistics regarding a reference model of the fiducial body. The statistics regarding the reference model of the fiducial body may include surface or volume information about the reference model.

The computer instructions may configure a data processor to segment a part of the fiducial body in a three-dimensional volume representation of the at least a part of the fiducial body in a scanned image to obtain a segmented fiducial body region. The computer instructions may further configure the data processor to align the segmented fiducial body region with the reference model. The computer instructions may further configure the data processor to determine a mapping transformation between the anatomical region or the fiducial body and the three-dimensional volumetric representation of the interior of the anatomical region and the fiducial body.

The computer instructions may further configure the computer readable storage medium to store the mapping transformation determined by the data processor.

The computer instructions may configure a receiving module to receive a known spatial relationship between at least one trackable marker and a fiducial body when the at least one trackable marker is attached to the fiducial body. The computer instructions may further configure the memory module to store the known spatial relationship.

The computer instructions may configure a pose tracking apparatus to determine a pose of the trackable marker attached to the fiducial body, wherein the fiducial body is rigidly fixed to the formed appliance, and wherein the formed appliance is attached to the anatomical region.

The computer instructions may configure the data processor to track a pose of an anatomical region displaceable in a coordinate reference frame and determine displacement of at least a portion of the anatomical region in the scanned image based on the pose of the trackable marker, the spatial relationship of the at least one trackable marker to the fiducial body and the mapping transformation between the fiducial body and the three-dimensional volumetric representation of the fiducial body and the interior of the anatomical region.

In some embodiments, the computer instructions may configure the pose tracking apparatus to dynamically measure a pose of an instrument pointing to locations in the interior of the anatomical region relative to the fiducial body. In such embodiments, the computer instructions may configure the data processor to mark the locations pointed to by the instrument on the three-dimensional volume representation of the interior of the anatomical region based on the mapping transformation.

The present invention has been described here by way of example only, and what has been described above has been intended to be illustrative of the invention and non-limiting. The exemplary advantages discussed above may not manifest in all embodiments of the invention. Various modification and variations may be made to these exemplary embodiments without departing from the spirit and scope of the invention, which is limited only by the appended claims.

We claim:

1. A method for registering an anatomical region with a scanned image of the anatomical region, the method comprising:

pressing a mouldable appliance against a surface of the anatomical region or a facsimile thereof to shape the mouldable appliance to conform to a surface geometry of the anatomical region to provide an intermediate appliance;

hardening the intermediate appliance to retain an appliance geometry shaped to mate with the surface geometry of the anatomical region to provide the formed appliance wherein the formed appliance resists deformation;

providing a fiducial body attached to the formed appliance such that the fiducial body is rigidly fixed to the formed appliance and is configured to be scannable to provide a three-dimensional volume representation of the fiducial body distinguishable from a three-dimensional volume representation of the anatomical region and the fiducial body being shaped and attached to the formed appliance such that the orientation of the fiducial body is uniquely determinable based at least in part on a degree of asymmetry of the fiducial body;

attaching the formed appliance with the fiducial body attached thereto to the anatomical region such that when attached to the anatomical region the formed appliance resists displacement relative to the anatomical region;

scanning the anatomical region with the formed appliance attached thereto and the fiducial body attached to the formed appliance to obtain a three-dimensional volume representation of at least a part of the fiducial body and an interior of the anatomical region in a scanned image;

segmenting the part of the fiducial body in the three-dimensional volume representation of the at least a part of the fiducial body in the scanned image to obtain a segmented fiducial body region;

aligning the segmented fiducial body region with a reference model of the fiducial body to obtain a mapping transformation; and operating a data processor to map locations in an interior of the anatomical region to corresponding locations in the three-dimensional volume representation of the interior of the anatomical region based on the mapping transformation.

2. The method as defined in claim 1, further comprising, when the formed appliance is mated with the surface of the anatomical region, positioning an instrument to point to locations in the interior of the anatomical region, operating a pose-tracking apparatus to measure the pose of the instrument relative to the fiducial body, and operating a data processor to mark the locations pointed to by the instrument on the three-dimensional volume representation of the interior of the anatomical region based on the mapping transformation.

3. The method as defined in claim 2 wherein the formed appliance is separated from the anatomical region following the scanning and repositioned to mate its surface prior to positioning the instrument.

4. The method as defined in claim 2, further comprising:
providing at least one trackable marker, wherein the at least one trackable marker is attached to the fiducial body; and
wherein the spatial relationship of the at least one trackable marker to the reference model of the fiducial body is stored in a format accessible to the data processor; and
the data processor uses this spatial relationship in marking the locations.

5. The method as defined in claim 2, wherein after operating the tracking apparatus to determine the pose of the trackable marker attached to the fiducial body attached to the anatomical region, the method further comprises detaching the at least one trackable marker from the fiducial body and re-attaching the at least one trackable marker to a different fiducial body, the different fiducial body being attached to a different formed appliance having a different appliance geometry shaped to mate with a different surface geometry of at least a portion of a different anatomical region.

6. The method as defined in claim 1 wherein the aligning of the segmented fiducial body region with a reference model of the fiducial body to obtain a mapping transformation comprises operating a data processor to execute an algorithm for registration of volume-occupying regions.

7. The method as defined in claim 4 wherein the trackable marker is attached to the fiducial body following the scanning and prior to positioning the instrument.

8. The method as defined in claim 1, wherein, the fiducial body comprises aluminum or titanium, and canning the anatomical region with the formed appliance attached thereto comprises CT scanning of the anatomical region with the formed appliance attached thereto.

9. The method as defined in claim 1 wherein
the mouldable appliance comprises a thermoplastic sheet; and
pressing the mouldable appliance against the anatomical region or a model of the anatomical region to shape the mouldable appliance to conform to the surface geometry of the anatomical region to provide the intermediate appliance comprises heating the mouldable appliance to render it soft and malleable and then pressing the thermoplastic sheet against the anatomical region or the model of the anatomical region.

10. The method as defined in claim 1, wherein attaching the formed appliance with the fiducial body attached thereto to the anatomical region precedes attaching the at least one trackable marker to the fiducial body.

11. The method as defined in claim 1, wherein
the anatomical region comprises human jaw;
pressing a mouldable appliance against the anatomical region or a model of the anatomical region to shape the mouldable appliance to conform to a surface geometry of the anatomical region to provide an intermediate appliance comprises placing a mouldable appliance around the human teeth or a facsimile of the human teeth to conform to the surface geometry of the human teeth to provide an intermediate appliance; and
hardening the intermediate appliance to retain the appliance geometry shaped to mate with the surface geometry of the anatomical region to provide the formed appliance comprises hardening the intermediate appliance to retain the appliance geometry shaped to mate with the surface geometry of the human teeth to provide the formed appliance.

12. The method as defined in claim 1, wherein the fiducial body has a plurality of symmetrical orientations, and wherein aligning the segmented fiducial body region with a reference model of the fiducial body comprises obtaining an approximate orientation of the anatomical region in the three-dimensional volume representation and selecting one of the symmetrical orientations based on the approximate orientation.

13. The method as defined in claim 1, wherein the fiducial body is asymmetrical such that any one orientation of the fiducial body is distinguishable from any other orientation of the fiducial body due to the asymmetry.

14. An apparatus for registering an anatomical region with a scanned image of the anatomical region, the apparatus comprising:
a mouldable appliance configured for moulding into a formed appliance having an appliance geometry shaped to mate with a surface geometry of at least a portion of the anatomical region, wherein the formed appliance resists deformation and when attached to the anatomical region, the formed appliance resists displacement relative to the anatomical region; and
a fiducial body, the fiducial body being attached to the mouldable appliance and shaped such that an orientation of the fiducial body relative the anatomical region is uniquely determinable, and wherein when the mouldable appliance is moulded into the formed appliance, the fiducial body becomes rigidly fixed to the formed appliance such that the fiducial body is in a fixed spatial relationship with the formed appliance, wherein at least part of the fiducial body is detectable to a scanner conducting a scan of the anatomical region to provide a three-dimensional volume representation of the fiducial body in a scanned image.

15. The apparatus according to claim 14, wherein the apparatus further comprises at least one trackable marker, wherein the at least one trackable marker is attachable to the fiducial body at an attachment location such that when the at least one trackable marker is attached to the fiducial body at the attachment location a spatial relationship of the at least one trackable marker to the fiducial body is fixed.

16. The apparatus according to claim 15, wherein the at least one trackable marker is configured to be detachable from the fiducial body and re-attachable to a different fiducial body.

17. The apparatus according to claim 14 wherein the fiducial body comprises a scan detectable material for enabling the at least part of the fiducial body to be detectable by the scanner conducting a scan such that upon scanning the anatomical region with the formed appliance attached thereto and the fiducial body attached to the formed appliance to provide the scanned image, the interior of the anatomical region underlying the formed appliance is distinguishable from the fiducial body in the scanned image.

18. The apparatus according to claim 14, wherein the fiducial body comprises aluminum or titanium for enabling the fiducial body to be detectable by the scanner conducting a CT scan, such that upon scanning the anatomical region with the formed appliance attached thereto and fiducial body attached to the formed appliance to provide the scanned image, the interior of the anatomical region underlying the formed appliance is distinguishable from the fiducial body in a CT scanned image.

19. The apparatus according to claim 14, wherein the mouldable appliance comprises a thermoplastic sheet, the thermoplastic sheet being configured to become soft and malleable upon heating to a transition temperature such that the thermoplastic sheet, when rendered soft and malleable by heating to the transition temperature, is pressable against the anatomical region to obtain the appliance geometry without injuring the anatomical region or causing pain when pressed against the anatomical region due either to a force of pressing or the heated thermoplastic sheet being at the transition temperature.

20. The apparatus according to claim 19, wherein the thermoplastic sheet is formed of a PolyForm® material such that the thermoplastic sheet is configured to become soft and malleable upon being heated to the transition temperature.

21. The apparatus according to claim 14, wherein the fiducial body is configured to be asymmetrical in shape such that any one orientation of the fiducial body is distinguishable from any other orientation of the fiducial body due to the asymmetry.

22. The apparatus according to claim 14, wherein the fiducial body is configured to have a plurality of symmetrical orientations such that one of the symmetric orientations is uniquely distinguishable based on the spatial relationship between the fiducial body and the anatomical region.

* * * * *